United States Patent [19]

Carey

[11] Patent Number: 5,804,218
[45] Date of Patent: Sep. 8, 1998

[54] METHODS AND COMPOSITIONS FOR INHIBITING ENTEROHEPATIC CYCLING OF BILIRUBIN

[75] Inventor: Martin C. Carey, Wellesley, Mass.

[73] Assignee: Brigham & Women's Hospital, Inc., Boston, Mass.

[21] Appl. No.: 924,055

[22] Filed: Aug. 28, 1997

[51] Int. Cl.$^6$ .......................... A61K 33/32; A61K 31/315
[52] U.S. Cl. ............................................. 424/641; 514/494
[58] Field of Search ............................... 424/641; 514/494

[56] References Cited

U.S. PATENT DOCUMENTS

| | | | |
|---|---|---|---|
| 4,548,922 | 10/1985 | Carey et al. | 514/4 |
| 4,746,508 | 5/1988 | Carey et al. | 514/2 |
| 4,959,358 | 9/1990 | Carey et al. | 514/171 |
| 5,589,504 | 12/1996 | Dannenberg | 514/456 |

OTHER PUBLICATIONS

Mendez–Sanchez et al., Inhibition of the Enterohepatic Cycling of Unconjugated Bilitubin by Zinc Abstract), 1997.
Gilbertsen, A.S., et al. "Enterohepatic circulation of Unconjugated Bilirubin in Man", *Nature,* (1962), 196:141–142.
Ulstrom, R.A. and Eisenklam, E., "The Enterohepatic Shunting of Bilirubinin in the Newborn Infant", *J. Pediatr,* (1964), 65(1):27–37.
Odell, G.B., "'Physiologic', Hyperbilirubinemia in the Neonatal Period", *N Engl J Med,* (1967), 277(4): 193–195.
Poland, R.L. and Odell, G.B., "Physiologic Jaundice: The Enterohepatic Circulation of Bilirubin", *N Engl J Med.* (1971), 284(1):1–6.
Poland, R.L., et al., "High Milk Lipase Activity Associated with Breast Milk Jaundice", *Pediatr Res,* (1980), 14(12):1328–1331.
Gourley, G.R., et al., "The Effect of Saccharolactone on Rat Intestinal Absorption of Bilirubin in the Presence of Human Breast Milk", *Pediatr Res,* (1989), 25(3):234–238.
Alonso, E.M., et al., "Enterohepatic Circulation of Nonconjugated Bilirubin in Rats Fed with Human Milk", *J Pediatr,* (1991), 118(3):425–430.
Gourley, G.R., et al., "The Effect of Diet on Feces and Jaundice During the First 3 Weeks of Life", *Gastroenterology,* (1992), 103:660–667.
R. Broderson and L.S. Hermann, "Intestinal Reabsorption of Unconjugated Bilirubin", The Lancet, (Jun. 8, 1963) 1242.

*Primary Examiner*—Kevin E. Weddington
*Attorney, Agent, or Firm*—Wolf, Greenfield & Sacks, P.C.

[57] ABSTRACT

Methods and compositions for removing bilirubin from the gastrointestinal tract are described. The compositions contain a zinc salt in a form that is insoluble in the gastrointestinal tract. The methods and compositions are useful for treating patients that have disorders associated with an elevated concentration of bilirubin including, for example, gallstone related disorders.

20 Claims, 4 Drawing Sheets

METHODS AND COMPOSITIONS FOR INHIBITING ENTEROHEPATIC CYCLING OF BILIRUBIN

GOVERNMENT SUPPORT

This invention was made in part under government support under Grant Nos. DK 36588 and DK 34854 from the National Institutes of Health. The U.S. government may have certain rights in this invention.

RELATED APPLICATIONS

This application is a continuation-in-part of provisional U.S. patent application Ser. No. 60/026,745, filed on Sep. 26, 1996, entitled METHODS AND COMPOSITIONS FOR INHIBITING ENTEROHEPATIC CYCLING OF BILIRUBIN, the disclosure of which is incorporated herein by reference.

FIELD OF THE INVENTION

This invention relates to methods and compositions for inhibiting the enterohepatic cycling of bilirubin by adsorbing soluble bilirubin from the gastrointestinal tract. In particular, the invention relates to the use of zinc salts to adsorb soluble bilirubin from the gastrointestinal tract.

BACKGROUND OF THE INVENTION

Bilirubin is a breakdown product of heme that typically forms as a result of erythrocyte destruction. Bilirubin normally circulates in the plasma complexed with albumin, is taken up by the liver cells and conjugated therein to form bilirubin mono- and diglucuronides, water-soluble pigments that are excreted in bile. In general, patients with abnormal bilirubin metabolism are classified on the basis of increased bilirubin turnover, decreased bilirubin clearance and combinations of the foregoing mechanisms. Abnormal bilirubin metabolism is manifested by: (1) increased pigment production, (2) reduced hepatic uptake of bilirubin, (3) impaired hepatic conjugation, and (4) decreased excretion of the conjugated pigment from the liver into bile. In the adult, chronic overproduction of bilirubin may lead to the formation of gallstones, particularly "pigment stones", i.e., stones formed primarily of calcium bilirubinate and containing less than 20% cholesterol.

In the United States, it is estimated that between 16 to 20 million persons have gallstone disease. Gallstones are divided into two main types: cholesterol stones and pigment stones. Cholesterol stones account for 70%–80% of the total gallstones in the United States; pigment stones account for the remaining 20%–30%. The presence of increased levels of unconjugated bilirubin in bile is believed to result in bilirubin precipitation as calcium salts and the aggregation of calcium bilirubinates to form pigment stones, as well as to form a nucleus for the formation of cholesterol gallstones. Chronic hemolytic states and alcoholic liver disease are associated with an increased incidence of gallbladder pigment stones. (See, e.g., *Harrison's Principles of Internal Medicine*, 12th Edition, eds. J. Wilson, et al., McGraw-Hill, Inc., New York, N.Y. (1991), Chapter 258 for a discussion of the diseases of the gall bladder and bile ducts).

Treatment for gallstones includes surgical removal, gallstone dissolution (e.g., oral bile acid therapy) and lithotripsy. In general, oral bile acid therapy is ineffective in dissolving pigment gallstones, radiopaque or calcified gallstones, and gallstones greater than approximately 1.5 cm in diameter. Lithotripsy (e.g., extracorporeal shock wave therapy) also is relatively ineffective in shattering pigment stones and is further limited in the size of the gallstones that can be disintegrated using this type of treatment.

In view of the foregoing, a need still exists to develop improved therapeutic methods for the prevention and treatment of gallstones and other disorders that are associated with elevated serum bilirubin. In particular, a need still exists for the prevention and dissolution of pigment stones which have a composition and/or size that are not readily treatable using existing non-surgical therapies. Such improved methods would prevent the information or growth of all types of gallstones and, thereby, prevent or reduce the incidence of gallstone-related complications.

SUMMARY OF THE INVENTION

Applicant has discovered that the gastrointestinal absorption of bilirubin, and consequently, high serum and biliary levels of bilirubin resulting in pigment stone formation, can occur only under the following conditions: (1) if bilirubin is deconjugated rapidly; and (2) if unconjugated bilirubin remains in solution in the gastrointestinal lumen. Of these factors, bile salt solubilization of unconjugated bilirubin ranks as one of the most important factors favoring its passive gastrointestinal absorption. Increased intestinal absorption of bilirubin results in high biliary levels and, consequently, sets the foundation for the formation of cholesterol stones and pigment stones. Conversely, a reduction in the intestinal absorption of bilirubin, presumably, will result in reduced biliary and plasma levels and a decreased risk of gallstones and pigment stones.

The experiments described herein substantiate applicant's hypothesis that the binding of unconjugated bilirubin in the gastrointestinal lumen to insoluble zinc salts reduces bilirubin reabsorption by the intestine. In particular, the experiments described herein demonstrate that zinc salts, at physiological pH, adsorb unconjugated bilirubin essentially completely from unsaturated bile salt micellar solutions and, thereby, suppress biliary bilirubin secretion in vivo. These results suggest that zinc salts are useful at physiological pH to inhibit the enterohepatic cycling (i.e., from cecum/colon to liver) of unconjugated bilirubin. Accordingly, applicant's discovery has resulted in a novel approach to preventing and treating gallstone and pigment stone formation, namely, by removing soluble bilirubin from the intestinal lumen as a means for reducing gallstone and pigment stone development and preventing the disorders that are incident to gallstone/pigment stone formation. Thus, the methods and compositions of the invention are useful for the prevention and treatment of disorders that are secondary to bile salt malabsorption.

According to one aspect of the invention, a method for removing bilirubin from a patient by adsorption of a soluble bilirubin in the gastrointestinal tract is provided. The method involves orally administering to the patient, a composition containing a zinc salt. The zinc salt is present: (I) in a therapeutically effective amount (i.e., an amount that is sufficient to reduce the concentration of bilirubin in the gastrointestinal tract to a normal concentration as manifested by a normal serum bilirubin concentration and/or a normal biliary bilirubin concentration), and (ii) in a form that is insoluble in the gastrointestinal tract. By "insoluble" it is meant that when ingested in therapeutically effective amounts, the zinc salt remains substantially intact so that it can transport bound bilirubin out of the body.

In general, a reduction in the amount of bilirubin in the gastrointestinal tract is manifested by a reduction in the concentration of bilirubin that is present in the serum or bile of the patient to whom the zinc salt is administered. An object of the therapy is to remove bilirubin from the patient until the patient's serum and biliary bilirubin concentrations fall within a normal range. Normal bilirubin concentration ranges and methods for measuring the concentration of bilirubin in serum and bile are known to those of ordinary skill in the art. (See, e.g., the Examples; U.S. Pat. No. 5,262,304, "Method for Optical Measurement of Bilirubin and Reagent Therefor", issued to Taniguchi; and *Harrison's Principles of Internal Medicine*, 12th Edition, eds. J. Wilson, et al., McGraw-Hill, Inc., New York, N.Y. (1991) for a discussion of the normal bilirubin concentration ranges and for exemplary methods for determining the concentration of bilirubin in serum and bile.)

The zinc salt is administered to the patient in any suitable form known to one of ordinary skill in the art for administering a therapeutic agent to the gastrointestinal tract with the provision, that the form remains substantially insoluble in the gastrointestinal tract. In the preferred embodiments, the zinc salt is orally administered to the patient. For example, the zinc salt, together with a pharmaceutically acceptable carrier, can be contained in a delivery vehicle (e.g., a tablet having an enteric coating, a pH sensitive delivery vehicle) that releases the zinc salt under the physiological conditions of the gastrointestinal tract. Preferably, the zinc salts are present in the composition in a form that releases the zinc salt under the conditions of physiological pH of the distal gastrointestinal tract (from about pH 7.0 to about pH 9.0). Thus, the invention provides a method of treatment which minimizes the release of the zinc salt in the stomach (thereby minimizing irritation that may be attributed to this therapeutic agent) and maximizes the delivery of the zinc salt to the distal gastrointestinal tract.

The compositions and methods of the invention are useful for treating a patient that has a disorder which is mediated by an excessive amount of a soluble form of bilirubin in the gastrointestinal tract. An excessive amount of soluble bilirubin refers to an amount of bilirubin that is greater than the concentration of bilirubin that would be found in the intestinal tract of an individual who has a normal serum or bile bilirubin concentration. Thus, an excessive amount of soluble bilirubin in the gastrointestinal tract is manifested by a serum and/or bile bilirubin concentration that is greater than a normal bilirubin concentration in these fluids. Normal serum bilirubin concentration ranges and methods for measuring the same are well known to one of ordinary skill in the art and can be obtained by consulting a medical textbook. (See, e.g., Harrison).

In a particularly preferred embodiment, the method of the invention involves selecting a patient having a disorder that is mediated by an excessive amount of an unconjugated form of bilirubin in the gastrointestinal tract, e.g., by identifying an adult patient having a total serum bilirubin concentration that is greater than about 34.0 $\mu$mol/L (2 mg/dL). More preferably, the adult or neonate patient has a serum bilirubin concentration from about 34.0 to about 170 $\mu$mol/L; most preferably, the patient serum bilirubin concentration is from about 34.0 to about 85 $\mu$mol/L. Alternatively, or additionally, the patient can be selected on the basis of an elevated biliary bilirubin concentration. Applicant has determined that normal adult gallbladder bile bilirubin concentrations fall within the range of about 700 $\mu$mol/L to about 3000 $\mu$mol/l. Thus, in a particularly preferred embodiment of the invention, the method involves selecting an adult patient having a gallbladder bile bilirubin concentration from about 3000 $\mu$mol/L to about 9000 $\mu$mol/L, i.e. at least about two- to three-fold greater than the normal gallbladder bile bilirubin concentration.

As used herein, a "patient" is a human, nonhuman primate, horse, cow, sheep, goat, dog, cat, or rodent. The invention is particularly directed to the treatment of humans having elevated serum and/or biliary bilirubin concentrations. Most preferably, the compositions and methods of the invention are intended for the treatment of adult humans and in particular, adult humans who have gallstone disease or a predisposition to gallstone disease, a bile salt malabsorption disorder, Crohn's disease, and/or other disorders associated with elevated serum and/or biliary bilirubin concentrations.

The zinc salts of the invention are delivered to the gastrointestinal lumen and are present therein in a therapeutically effective amount to treat the disorder. To accomplish this objective, the zinc salts for removing bilirubin from solution preferably are contained in a delivery vehicle that releases the zinc salt under the pH conditions of the intestinal lumen (from about pH 7.0 to about pH 9.0). Thus, the invention provides a method of treatment which minimizes the release of the zinc salt in the stomach (thereby minimizing irritation that may be attributed to the salt) and maximizes the delivery of the zinc salt to the intestinal lumen. Such pH-sensitive delivery vehicles and coatings are well-known to those of ordinary skill in the art and can be adapted for delivering the salts disclosed herein with no more than routine experimentation. In general, a therapeutically effective amount of zinc salt that is useful for treating the condition is an amount that is sufficient to reduce the concentration of bilirubin in the intestinal tract to within a normal bilirubin concentration range, e.g., as manifested by a serum and/or biliary bilirubin concentration that falls within a range that is clinically accepted as normal.

According to a related aspect of the invention, a method for decreasing a serum bilirubin and/or a biliary bilirubin concentration in a patient is provided. This aspect of the invention is based upon Applicant's discoveries that: (1) zinc salts can remove bilirubin from bile salt micelles under physiological pH conditions and (2) bile salt solubilization of diacidic unconjugated bilirubin ranks as the most important factor for the passive gastrointestinal absorption of bilirubin. According to this aspect of the invention, a composition including a zinc salt is administered to a patient in need thereof. The zinc salt is present in a form that is insoluble in the gastrointestinal tract and that, preferably, is coated with or contained within, a pH sensitive delivery vehicle as described above. Preferably, the zinc salt is present in an amount sufficient to reduce the concentration of bilirubin in the serum and/or in the bile to within a range that is clinically accepted as normal. In general, the amount of zinc salt that is sufficient to reduce the concentration of bilirubin in the serum and/or bile to within normal bilirubin concentration ranges for these body fluids will depend upon the extent to which the gastrointestinal bilirubin concentration is elevated. The person of ordinary skill in the art can determine the dosage levels and frequency of administration of the zinc salts in accordance with standard practice.

According to yet another aspect of the invention, a pharmaceutical composition is provided. The composition includes: (1) zinc salt; and (2) a pharmaceutically acceptable carrier. The zinc salt is present in the composition (I) in an amount sufficient to reduce an elevated serum or biliary bilirubin concentration to a normal serum or biliary bilirubin concentration and (ii) in a form that is insoluble in the gastrointestinal tract. The pharmaceutical composition can be sterile and can be formulated in a unit dosage in an amount effective for treating a condition that is mediated by an excessive concentration of bilirubin in the gastrointestinal tract. As used herein, "treating" means preventing the onset of, slowing the progression of, or eradicating the existence of the condition being treated, such as a gallstone disorder. Successful treatment is manifested by a reduction in the serum and/or biliary bilirubin concentrations to within normal levels. The pharmaceutical compositions can be formulated as any suitable preparation. In the preferred embodiments, the composition is formulated to be suitable for oral administration. Optionally, the pharmaceutical compositions contain a pharmaceutically acceptable carrier for oral administration, e.g., a sugar such as maltose, or other stabilizing agents. In the preferred embodiments, the pharmaceutical composition is contained in a delivery system that releases the zinc salt in the gastrointestinal tract, such as an enteric coated tablet or capsule, or in a pH sensitive delivery vehicle. Preferably, the delivery vehicle is designed and constructed to deliver the agent (i.e., release the agent) at a pH between about 7.0 and about 9.0. Such biocompatible delivery systems are well known to those of ordinary skill in the art.

According to yet another aspect of the invention, a method for forming a medicament is provided. The method involves placing a therapeutically effective amount of a zinc salt, as defined herein, in a pharmaceutically acceptable carrier, wherein the zinc salt is a form that is insoluble in the gastrointestinal tract. Preferably, the medicament is formulated in a single dosage for oral administration.

These and other aspects of the invention, as well as various advantages and utilities, will be more apparent with reference to the detailed description of the preferred embodiments and to the accompanying drawings.

All references, patent publications and patents identified in this disclosure are incorporated in their entirety herein by reference.

DETAILED DESCRIPTION OF THE INVENTION

Figure 1:
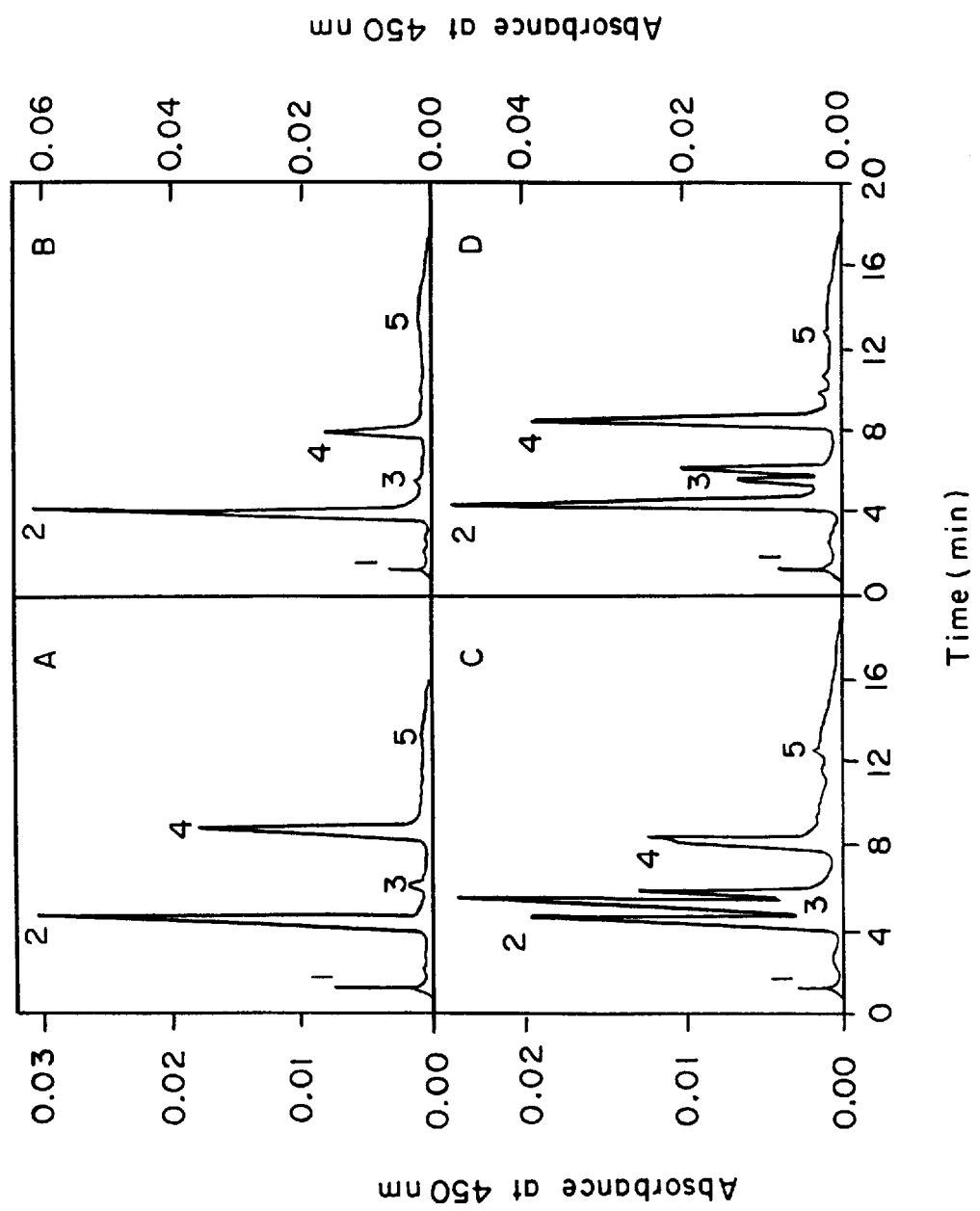
FIG. 1: Elution patterns of bile pigments in rat bile (A=450 nm) by high performance liquid chromatography (HPLC) during 0–15 min of a biliary washout performed 3 days following (A) sham laparotomy, (B,C) ileectomy and (D) distal jejunectomy. Methods and identification of peaks were by the procedures of Spivak and Yuey (32): 1. solvent peak; 2. bilirubin diglucuronide (BDG); 3. bilirubin monoglucuronide-monoglucoside (BMGGl); 4. two isomers of bilirubin monoglucuronide (BMG); 5. unconjugated bilirubin (UCB). Increased levels of bilirubin monoglucuronide-glucoside (BMGGl) (peak #3) were observed in about half of the ileectomized c) and distal jejunectomized (D) animals. Increased BMG peaks (#4) were highly variable. Note differences in ordinate scales between panels A/C and B/D.

A brief summary of bilirubin metabolism is provided to better understand the physiological processes that play a role in mediating bilirubin concentrations in serum and bile and the types of disorders that can be treated in accordance with the methods and compositions of the invention. The sources and precursors of bilirubin and the steps in its subsequent metabolism and excretion are described in detail in Harrison's Principles of Internal Medicine, 12th Edition, Eds. J. Wilson, et al., McGraw-Hill, Inc., New York, N.Y. (1991), Chapter 47.

Bilirubin is present in two principle forms: unconjugated bilirubin and conjugated bilirubin. "Unconjugated" bilirubin is released into the plasma where it becomes tightly bound to albumin. Unconjugated bilirubin is dissociated from albumin, enters the liver, and is converted to a water-soluble derivative prior to its excretion into bile. Solubilization of unconjugated bilirubin is a two step process in which bilirubin is conjugated sequentially to one or two molecules of glucuronic acid to form bilirubin glucuronides. The conversion of bilirubin glucuronides (water soluble) to unconjugated bilirubin (water insoluble) takes place in the distal small intestine and colon and is mediated principly by the beta-glucuronidase of bacteria. The beta-glucuronidase (also present in tissue and breast milk) cleaves the uronic acid groups from the bilirubin glucuronide to form the water insoluble derivative. This "unconjugated" bilirubin precipitates in the gastrointestinal tract (including the colon) and is excreted. Alternatively or additionally, the "unconjugated" bilirubin is further modified by bacteria to form urobilinogens and is excreted. In this manner, excessive bilirubin is removed from the body and disorders associated with elevated serum bilirubin levels (e.g., gallstone disease) are prevented.

If, however, bilirubin is "deconjugated" (i.e. one or more of the uronic acid groups are removed) at a place in the intestine where there is an abnormally high concentration of bile salts, the deconjugated bilirubin is solubilized by the bile salts and is not immediately excreted. It is believed that the principle route by which deconjugated bilirubin is solubilized involves sequestering by bile salt micelles; however, bilirubin also can be maintained in solution by bile salt monomers at concentrations that are less that the concentration necessary for bile salt micelle formation (also referred to as the "critical micellar concentration" or "CMC"). In general, the CMC ranges from about one to about five mM (1 g/dL=20 mM). Thus, it is proposed that elevated bile salt concentrations result in bile salt micelle formation in the gastrointestinal tract and in the sequestering of deconjugated bilirubin in the hydrophobic core of such micelles. Once bilirubin is sequestered in a bile salt micelle or attached to a bile salt monomer, the bilirubin becomes available for passive absorption by the lining of the intestine and thereafter, enters and is subject to the enterohepatic circulation. Accordingly, disorders of bile salt adsorption (leading to elevated bile salt concentrations in the gastrointestinal tract) are believed by Applicant to be the principle cause of elevated levels of bilirubin in the gastrointestinal tract, in bile and in serum. The compositions of the invention, by removing bilirubin from solution in the gastrointestinal tract (including the proximal and distal small intestine and the large intestine), are useful for treating any condition that is mediated by an elevated concentration of bilirubin and/or bile salts in the gastrointestinal tract.

The instant disclosure provides compositions and methods for removing bilirubin from a patient by adsorption of soluble bilirubin in the gastrointestinal tract. The invention is based upon the surprising discovery that insoluble zinc salts at physiological pH adsorb unconjugated bilirubin essentially completely from unsaturated bile salt micellar solutions in vitro and suppress biliary bilirubin secretion in an animal model system in vivo. As a result of the foregoing discoveries, methods and compositions are provided that make use of zinc salts for adsorbing bilirubin from the gastrointestinal tract. The methods and compositions of the invention are useful for modulating the enterohepatic circulation of bilirubin and, thereby, reducing the concentration of bilirubin in serum and bile.

According to one aspect of the invention, a method for removing bilirubin from a patient by adsorption of soluble bilirubin in the gastrointestinal tract is provided. The method involves orally administering to the patient, a composition including a zinc salt. The zinc salt is present in the composition (I) in a therapeutically effective amount and (ii) in a form that is insoluble in the gastrointestinal tract. The method is useful for treating a patient that is diagnosed as having a disorder that is mediated by an excessive amount of a soluble form of bilirubin (predominantly, unconjugated bilirubin) in the gastrointestinal tract. Typically, such conditions are diagnosed by observing a concentration of bilirubin in the serum or bile that is greater than the established normal bilirubin concentration range found in these fluids. Exemplary disorders that can be treated in accordance with the methods of the invention include gallstone disorders, disorders of bile salt absorption and Crohn's disease. Additional disorders that are believed to be mediated by an elevated concentration of serum and/or biliary bilirubin are described in more detail below. In general, diseases that can be treated in accordance with the methods of the invention include gallstone diseases, i.e., diseases associated with a high prevalence of gallstones, including: (1) inflammatory bowel disease (Crohn's disease); (2) Cystic Fibrosis syndrome; (3) alcoholic cirrhosis; (4) diets with high levels of starch such as rice diets as in the Orient; (5) congenital mutations of the ileal bile acid transporter; (6) ileal bypass for obesity and hyperlipidemia; and (7) pharmaceutical agents that inhibit the ileal bile acid transporter (IBAT inhibitors). Jaundice also can be treated in accordance with the methods and compositions of the invention. In particular with respect to jaundice, if the liver is immature or dysfunctioning from disease, it is believed that the enterohepatic cycling of bilirubin results in an elevated serum bilirubin level which may be diagnosed as clinical jaundice. Typically, jaundice due to unconjugated bilirubin is characterized by a yellow discoloration of the skin, sclera or mucus membranes. Normal serum bilirubin concentration range from about 5 to 17 µmol/L (or 0.3 to 1.0 mg/dL), and most of this is unconjugated. The level of bilirubin at which jaundice becomes clinically evident varies, but in general, a total serum bilirubin concentration exceeding 34 to 43 µmol/L (2 to 2.5 mg/dL) is considered diagnostic of jaundice.

The results presented herein suggest that the methods and compositions of the invention can be used to treat a patient having one or more of the foregoing disorders by interrupting the enterohepatic circulation of bilirubin. As used herein, a "patient" is a human, nonhuman primate, horse, cow, sheep, goat, dog, cat, or rodent. The invention is particularly directed to the treatment of the adult humans having elevated serum and/or biliary bilirubin concentration. In particular, the invention is directed to the treatment of any mammal that is capable of forming cholesterol or pigment stones as a result of excess bilirubin in the gastrointestinal tract. Accordingly, "patient" embraces humans, livestock (e.g., horses) and other types of mammals. The preferred patient is a human, more preferably, an adult human.

It is believed that a variety of zinc salts can be used as therapeutic agents to interrupt the enterohepatic cycling of bilirubin in a patient. Zinc, the least toxic of the trace metals, can form a variety of salts that are useful for practicing the instant invention, provided that the zinc salt is non-toxic under the conditions of administration and remains substantially insoluble in the gastrointestinal tract. The zinc salts of the instant invention, are aqueous soluble at a pH less than pH 6.5 and are substantially insoluble (i.e., less than about 1.0% soluble) at a pH from about pH 6.5 to a pH of at least about pH 9.5. The pH of the gastrointestinal tract ranges aborally from about pH 6.0 to about pH 9.0 with the exception of a pH of about pH 2.0 to pH 4.0 in the stomach. Accordingly, the zinc salts of the instant invention are substantially insoluble in the gastrointestinal tract. Typically, the salts are observed to be in a flocculent form at a pH greater than about pH 6.5. Because the zinc salts remain substantially insoluble in the gastrointestinal tract and are excreted in the feces, relatively high concentrations of the zinc salt (i.e., 100 mg/day/70 kg body weight to 1000 mg/day/70 kg body weight) can be administered without toxic or other adverse effect.

The zinc salts that are suitable for administration to a human are commercially available or can be synthesized in accordance with standard procedures known to one of ordinary skill in the art. The negatively charged counter ions of the zinc salts may be organic ions, inorganic ions, or combinations thereof. The inorganic ions suitable for use in the invention include the halides (e.g., chloride), methacrylate phosphate, phosphite, carbonate, bicarbonate, sulfate, bisulfate, hydroxide, nitrate, persulfate, sulfite, and sulfide. Suitable organic ions include acetate, ascorbate, benzoate, citrate, dihydrogen citrate, hydrogen citrate, oxalate, succinate, and tartrate. The most preferred zinc salts are zinc sulfate, zinc gluconate, zinc acetate, and zinc aspartate. Zinc sulfate is the most preferred zinc salt for practicing the invention. Several zinc salts have been incorporated into pharmaceutical compositions for administration to a human, e.g., as vitamin supplements and as therapeutic agents for treating disorders relating to zinc deficiency. (See, e.g., U.S. Pat. No. 3,887,704, "Aqueous Zinc Solutions for Physiological Use", issued to Lichtenstein). Thus, the person of ordinary skill in the art is well acquainted with numerous zinc salts that can be administered to a human as dietary supplements and for treating disorders relating to zinc metabolism.

The zinc salts are screened for therapeutic activity in screening experiments (in vitro and/or in vivo) such as those described in the Examples. In particular, the Examples demonstrate that the in vitro screening assay in which zinc salt-mediated extraction of bilirubin from bile salt micelles is measured is predictive of an in vivo activity in the animal model system. Such screening experiments can be performed using routine experimentation (e.g., substituting an untested zinc salt, or other putative therapeutic agent such as activated charcoal) for a zinc salt having known activity in the screening assays. Those of ordinary skill in the art will readily know how to modify such screening experiments for the purpose of identifying additional zinc salts that fall within the scope of the invention. Accordingly, although the following description of the invention specifically refers to zinc salts, it is intended that other salts can be substituted for zinc salts in each aspect of the invention.

Although selected zinc salts may have been formulated as pharmaceutical preparations and as dietary supplements, the person of ordinary skill in the art would not have considered formulating such zinc salts in delivery vehicles that would be appropriate for delivering a therapeutically effective amount of the salt to the gastrointestinal tract to interrupt the enterohepatic circulation of bilirubin in humans. Moreover, because the prior art zinc salt formulations were intended, for the most part, as dietary supplements or for the treatment of zinc deficiencies in humans, such formulations contained relatively small amounts of the zinc salts (e.g., ranging from about 5 $\mu$g/dose to about 25 mg/dose). In general, such concentrations would not be effective for treating the conditions described herein. Accordingly, such preparations do not contain a therapeutically effective amount of the zinc salts as defined herein.

When used therapeutically, the compounds of the invention are administered in therapeutically effective amounts to treat a condition that is mediated by an above-normal concentration of bilirubin in the gastrointestinal tract. In general, a therapeutically effective amount means that amount necessary to delay the onset of, inhibit the progression of, ameliorate the symptoms of or halt altogether the particular condition being treated. More particularly, a therapeutically effective amount of the zinc salt of the invention is an amount which, when administered to the patient, causes a reduction in the bilirubin concentration of the gastrointestinal tract to within a normal bilirubin concentration range. Typically, this reduction is manifested by a corresponding reduction in the patient's serum and/or biliary bilirubin concentrations to a level that falls within a normal concentration range.

Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount typically varies from 0.01 mg/kg to about 300 mg/kg, preferably from about 0.1 mg/kg to about 200 mg/kg and most preferably from about 0.2 mg/kg to about 20 mg/kg, in one or more dose administrations daily, for one or more days. The therapeutically effective amount of the compounds of the invention is less than that amount that produces medically unacceptable side-effects.

In the particularly preferred embodiments, a therapeutically effective amount of a zinc salt for reducing the concentration of bilirubin in the gastrointestinal tract is an amount ranging from about 0.7 mg/kg to about 70 mg/kg. More preferably, the concentration of the therapeutic agent in the gastrointestinal tract is in the range of 5 mmol/L to about 20 mmol/L, and most preferably is in the range of about 5 mmol/L to about 10 mmol/L. In general, the compositions of the instant invention contain zinc salts that are present in amounts that are at least twice, and, more typically, at least five to ten-fold the amounts of zinc salts that are present in the pharmaceutical compositions of the prior art. However, the compositions can contain lesser amounts of the zinc salts, provided that the salt is contained in a delivery vehicle (e.g., a pH sensitive delivery vehicle) that can deliver substantially all of the zinc salt (i.e., at least 90%) directly to the gastrointestinal tract. It is preferred that at least 95% and, preferably, at least 99% of the zinc salt present in the pharmaceutical composition be delivered to the distal gastrointestinal tract.

In general, a reduction in the distal gastrointestinal tract bilirubin concentration is manifested by a corresponding reduction in the bilirubin concentration in the patient's serum and bile. Methods for measuring the concentration of bilirubin in serum and bile are well known to those of ordinary skill in the art. Thus, the invention also provides methods and compositions for decreasing a patient's serum and/or bile bilirubin concentration by adsorbing soluble bilirubin from the patient's gastrointestinal tract. Preferably, the zinc salt is present in the composition in an amount sufficient to reduce an elevated serum and/or an elevated biliary bilirubin concentration to a concentration that falls within a normal serum and/or biliary bilirubin concentration range.

Elevated biliary levels of bilirubin place a patient at risk for developing cholesterol and pigment gallstones. Accordingly, the instant invention is particularly useful for preventing or decreasing the incidence or growth of gallstones in adult humans. It is believed that frequent (daily) treatment will be most successful. In addition, if the transport and conjugation systems of the liver are not functioning correctly, such as from disease, inherited disfunction or immaturity (neonatal prematurity), then the re-absorbed bilirubin enters the systemic circulation and causes overt jaundice. Thus, any condition, surgical or medical, that causes increased entry of bile salts into the large intestine/colon/cecum will result in an elevated bilirubin concentration in the gastrointestinal tract. Such conditions and methods include surgical removal of the ileum and the use of high carbohydrate or cholesterol diets or drugs that provide chemical competition for bile salt receptors.

The experiments described in the Examples demonstrate that under certain conditions, unconjugated bilirubin can be absorbed from the large intestine to return by the portal vein to the liver and ultimately, excreted as bilirubin conjugates into the bile. In particular, the in vitro results demonstrate that flocculated zinc salts ($ZnSO_4$, $ZnCO_3$, $Zn(OOCCH_3)_2$) remove unconjugated bilirubin from micellar bile salt solutions under the pH conditions that would be present in the gastrointestinal tract. These results suggest that the zinc salt-mediated removal of bilirubin from bile salt micelles also likely occurs in the distal small and large intestine. Moreover, the in vivo results demonstrate that feeding $ZnCO_3$ to hamsters at a 1% dietary level results in decreased biliary bilirubin secretion and suggests that some enterohepatic cycling occurs in healthy animals, especially those animals which produce monoconjugated bilirubin predominantly. In summary, the in vitro and in vivo experiments described herein are predictive of the role played by insoluble zinc salts in modulating the enterohepatic circulation of bilirubin in man.

High levels of monoconjugate bilirubin also occur in patients with Gilbert's syndrome (a mild form of hereditary hyperbilirubinemia), and in alcoholic cirrhosis where there is an increased risk for pigment and other gallstone development. Thus, these conditions also can be treated in accordance with the methods of the invention. The methods and compositions of the invention also are useful for treating the enterohepatic cycling of bilirubin associated with inflammatory bowel condition of Crohn's type, where the ileum is severely diseased or has been removed for severe disease. The Examples show that in such conditions, the bilirubin levels in the gallbladder bile were significantly elevated compared to the bilirubin levels in the bile of controls that included (1) Crohn's disease patients without ileectomy; (2) patients with ulceration colitis; and (3) patients with gallstones. Although the unconjugated bilirubin concentrations typically were approximately 1% of the total in the control biles, the unconjugated bilirubin concentrations in Crohn's patients with ileectomy were increased to approximately 5% of the control bile values.

The pharmaceutical compositions of the invention contain a zinc salt and a pharmaceutically acceptable carrier. Preferably, the pharmaceutical composition is designed and constructed for oral administration to the patient. The zinc salt is present in the composition in an amount that is sufficient to reduce an elevated serum and/or biliary bilirubin concentration in a patient to a serum and/or biliary bilirubin concentration that falls within a normal range. The zinc salt is present in a form that is insoluble in the gastrointestinal tract. The pharmaceutically acceptable carrier is selected, in part, based upon the mode of delivery. In the preferred embodiments, the pharmaceutical composition is suitable for oral administration, e.g., a sugar (mannose) or other stabilizing agent can be admixed with the zinc salt. Alternatively or additionally, the zinc salt can be prepared as a solution or suspension (e.g., in sterile saline) and placed within a delivery vehicle (e.g., a capsule) for administration to the patient. More preferably, the above-described composition is contained in a delivery vehicle that preferentially releases the zinc salt in the gastrointestinal tract.

As used herein, a "delivery vehicle" refers to a material which mediates the delivery of the zinc salt to the gastrointestinal tract and its release therein. More preferably, the delivery vehicle mediates delivery/release of substantially all ($\geq 90\%$) of the zinc salt. Most preferably, the delivery vehicle mediates delivery/release of $\geq 95\%$ (preferably, $\geq 99\%$) of the zinc salt to the distal gastrointestinal tract.

The delivery vehicles of the invention, when used for oral administration, protect the zinc salt from solubilization and/or other degradation upon exposure to the acidic pH of the stomach. Thus, in a particularly preferred embodiment, the delivery vehicle releases the zinc salt at a pH greater than about pH 7.0, and more preferably, releases the zinc salt at a pH from about pH 8.0 to about pH 9.0. Such pH sensitive delivery vehicles are well known to those of ordinary skill in the art. The delivery vehicle can be a capsule, tablet or other common type of formulation, which includes an enteric coating that is substantially resistant to acidic pH (to minimize dissolution in the acidic environment of the stomach) and that is sensitive to basic pH (to promote dissolution in the basic environment of the gastrointestinal tract). By "resistant to acidic pH," it is meant that the enteric coating does not dissolve to a significant extent (i.e., less than 5% dissolution, more preferably, less than 1% dissolution and most preferably, less than 0.1% dissolution) in the acidic environment of the stomach. Conversely, by "sensitive to basic pH", it is meant that the enteric coating dissolves or otherwise breaks down to release its contents in the basic pH environment of the distal gastrointestinal tract. Such pH sensitive enteric coatings and delivery vehicles are well known to those of ordinary skill in the art and can be adapted for delivering the agents disclosed herein using no more than routine experimentation. (See, e.g., U.S. Pat. No. 5,356,625, "Microgranular Preparation Useful in the Delivery of Biologically Active Materials to the Intestinal Regions of Animals", issued to Ying ("Ying"); U.S. Pat. No. 5,171,580, "Orally-Pharmaceutical Preparations with Colon Selective Delivery", issued to Iamartino et al. ("Iamartino"); U.S. Pat. No. 4,983,401, "Sustained Release Pharmaceutical Preparations Having pH Controlled Membrane Coatings", issued to Eichel et al. ("Eichel"); and U.S. Pat. No. 4,832,958, "Galenic Forms of Prolonged Release Verapamil and Medicaments Containing Them", issued to Baudier et al. ("Baudier") delivery systems and methods of preparing same.) The relevant teachings from these patents are summarized below.

Ying describes compositions containing a core of a biologically active material. The core is encapsulated by a water soluble film that is covered by an enteric coating of either an alkali soluble, acid insoluble polymer or a high molecule weight polymer including fatty acids or other materials that are capable of being solubilized by intestinal juices. In general, the Ying compositions are designed to protect pH sensitive and other biologically active materials from contact with the stomach and releasing the contents in active form in the intestinal tract. The active materials may be immobilized by, for example, entrapment in a core of gel-like material or within a semi-permeable membrane. The entrapment of active materials within the core is performed in accordance with standard procedures, including e.g., admixing the active materials with agents capable of forming a gel under certain conditions to entrap the active agent therein. Exemplary gel forming agents include κ-carrageenan, alginic acid, gelatin, cellulose or its derivatives or various gel-forming synthetic polymers such as polyamides of Chitosan. The gel matrix containing the immobilized active material can be formed into microgranules of a desired particle size to enhance surface area and permit the rapid release of the active material from the delivery vehicle when it reaches the intestine.

Iamartino describes orally administrable pharmaceutical compositions containing an active ingredient that is released in the lower part of the gastrointestinal tract. The Iamartino compositions include three layers: (1) an inner layer containing an anionic copolymer which is soluble at a pH above 7.0 and a plasticizer; (2) an intermediate layer, containing a gelling polymer which swells to yield a thick gel layer; and (3) an outer layer, containing a gastro-resistant polymer that is able to dissolve quickly in the intestine. The inner layer may contain the active ingredient alone or in admixture with carrier materials or dispersed on the surface of a carrier particle. The inner layer anionic polymers include polymers derived from methacrylic acid and methyl methacrylate; exemplary inner layer plasticizers include polyethylene glycol, dibutylphthalate, diethylphthalate, triacetin, castor oil and citric acid esters. The amount of the inner layer is designed to achieve quick release of the active ingredient at sustained pH levels greater than about pH 7.0. The intermediate layer gelling polymers are polymer materials which easily swell in aqueous media at any pH. Exemplary gelling polymers include methyl cellulose, carboxymethylcellulose, hydroxypropylcellulose, hydroxypropylmethylcellulose, polyvinylalcohols, polyoxyethyleneglycols, polyvinylpyrrolidone or their mixture, preferably hydroxypropylmethylcellulose. According to Iamartino, the intermediate gelling polymer is applied on the first inner layer in an amount between about 10 to 40 percent by weight. The type and amount of the gel layer is selected to obtain a delay of about 2–4 hours. The combination of the gel layer with the pH sensitive inner layer ensures that during the intestinal transit time the enteric juice does not affect the inner layer. The gastroresistent polymer used in the outer layer is selected from the commonly used enteric materials such as cellulose acetate phthalate, hydroxypropylmethylcellulose phthalate, polyvinyl acetate phthalate, hydroxyethyl cellulose phthalate, cellulose acetate tetrahydrophthalate, preferably acrylic polymers such as the anionic copolymer derived from methacrylic acid and methylmethacrylate.

The process for making the Iamartino compositions involves coating a core containing the active ingredient with a three layer coating by spraying the respective coating solutions or dispersions in suitable solvents. The core is prepared according to known procedures. For example, the core can be prepared by granulation or by tableting. The core optionally contains pharmaceutically inert materials of the type normally used in pharmaceutical preparations such as polyssaccharides, microcrystalline cellulose and waxes. According to Iamartino, the coating inner layer is applied on the cores by conventional methods (e.g., spraying) an organic solution of the inner layer polymer, together with an appropriate plasticizer. The intermediate layer is applied on the inner layer by spraying a suitable solution or dispersion of the gelling polymers in a suitable solvent(s). The outer layer is applied by spraying a suitable solution of the gastro-resistant polymer onto the intermediate layer.

Eichel describes sustained release pharmaceutical compositions containing a core (including a drug) that is coated with a film forming polymer to form a pH controlled diffusion membrane. The compositions are formed into microparticles. Because the permeability of the membrane is pH controlled, the particles reportedly do not release significant amounts of the core drug in the stomach but slowly and steadily release the drug in the intestine.

Baudier describes pharmaceutical compositions consisting of microgranules (containing the Baudier active ingredient) that are coated with a microporous membrane. The membrane is formed from at least one insoluble acrylic or methacrylic polymer and a substance that is insoluble in the acid gastric medium but soluble in the intestine. Exemplary substances which satisfy these criteria include cellulose acetophthalate, polyvinyl acetophthalate, hydroxypropylmethyl cellulose phthalates, methyl vinyl ether/maleic anhydride) polymers, and C10 to C20 fatty acids. The Baudier compositions are formed using techniques known to one of ordinary skill in the art.

In summary, the art is replete with examples of delivery vehicles which can be used to contain the zinc salts of the invention for achieving the purposes of the invention. As the person of ordinary skill in the art will appreciate, the nature and thickness of the coatings of the delivery vehicle and the size of the core containing the zinc salt(s) governs the rate at which the zinc salt(s) become available in the gastrointestinal tract and the location within the tract at which the zinc salt(s) are released.

Although oral administration of the zinc salts is preferred, the invention embraces other modes for delivering the zinc salts to the gastrointestinal tract. Accordingly, the therapeutics of the invention can be administered to the patient using any conventional route, provided that the zinc salts are delivered to the gastrointestinal tract and remain substantially insoluble therein. For example, delivery vehicles such as pumps or implants that contain the pharmaceutical compositions of the invention can be implanted at the time of surgery for the controlled release of zinc salts following ileal resection. Techniques for preparing oral, implants and pump delivery systems are well known to those of skill in the art. Generally, such systems should utilize components which will not significantly impair the biological properties of the therapeutic. Those of skill in the art can readily determine the various parameters and conditions for producing oral, implant and pump formulations without resort to undue experimentation.

Preparations for administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's or fixed oils. Preservatives and other additives may also be present such as, for example, antimicrobials, anti-oxidants, chelating agents, and inert gases and the like.

Certain of the various objects and advantages of the invention are illustrated in the following examples. Numerous equivalents and embodiments will be apparent to those of ordinary skill in the art and are intended to be embraced by the appended claims.

The examples are presented below and are followed by what is claimed.

EXAMPLE 1

Bilirubin Cycles Enterohepatically After Ileal Resection in the Rat

Abbreviations Used: BS, bile salt; BW, body weight; BDG, bilirubin diglucuronide; BMG, bilirubin monoglucuronide; BMGG1, bilirubin monoglucuronide-monoglucoside; UCB, unconjugated bilirubin; EHC, enterohepatic circulation; HPLC, high-performance liquid chromatography.

Tables and References: The Tables and References for Example 1 are located at the end of this Example.

Abstract

BACKGROUND Contrary to previous beliefs, patients with ileal disease, resection or bypass are at increased risk of developing pigment gallstones, but the pathophysiological mechanism is unknown. AIMS We tested the hypothesis that ileectomy in the rat induces enterohepatic cycling of bilirubin. METHODS We performed ileectomy or sham operation in adult male Sprague-Dawley rats with several control procedures: no operation, ileal transection, proximal or distal jejunectomy, ileo-colonic transposition and ileo-cectomy. We measured bilirubin and bile salt secretion rates during acute (0–30 min) biliary washout performed at 3, 5, 8, and 11 days post-surgery and measured large intestinal bilirubin and bile salt concentrations as well as indices of hemolysis in blood. RESULTS Bilirubin secretion rates were increased significantly ($p<0.001$) 3 days following ileectomy, distal jejunectomy, ileo-colonic transposition and ileocecectomy compared with controls and no hemolysis occurred. Bile salt secretion rates following ileectomy increased significantly compared with sham operated rats, but decreased markedly following prevention of coprophagy, whereas bilirubin secretion rates remained elevated. At 8–11 days post-surgery, intestinal adaptation restored bile salt reabsorption to normal, and enterohepatic cycling of bilirubin was abolished. In ileectomized animals cecal levels of unconjugated bilirubin and bile salts were increased 5 to 8 fold, but in bile unconjugated bilirubin levels remained normal (<1%). CONCLUSIONS These results are consistent with the hypothesis that enterohepatic cycling of bilirubin occurs with bile salt malabsorption induced by ileectomy.

Introduction

Patients with ileal disease, resection or bypass (e.g. Crohn's disease, surgery for morbid obesity or hypercholesterolemia) are at increased risk for gallstone disease (1–3), whereas prevalence of cholelithiasis in patients with ulcerative colitis is comparable to the general population (2). It was believed that ileal dysfunction, which interrupts the enterohepatic circulation (EHC) of bile salts (BS), resulted in cholesterol supersaturated bile and cholesterol gallstone formation (4,5). Although acute biliary diversion may augment cholesterol saturation of bile, particularly in patients with preexistent defects in biliary lipid secretion (6), nonetheless, studies in both humans (6) and rhesus monkeys (7) have suggested that cholesterol supersaturation of bile is not sustained. Presumably, this occurs because of derepression of hepatic cholesterol 7α-hydroxylase activity, the rate limiting enzyme in cholesterol's conversion to BS (8). This concept is consistent with studies of Crohn's disease patients in Sweden showing that bile is either unsaturated with cholesterol, or significantly less saturated than controls (9,10).

In the ileectomized prairie dog, a cholesterol-rich diet leads to development of lithogenic bile and cholesterol gallstones (11), whereas a trace-cholesterol diet induces pigment gallstone formation (11–13). Microscopy and analysis of prairie dog bile after ileal-resection revealed calcium bilirubinate precipitates and small pigment gallstones as well as increased levels of calcium and total bilirubin, but normal cholesterol saturation indexes (12). Furthermore, Coyle and colleagues (14) showed that ileal bypass in the guinea pig also resulted in pigment gallstone formation. Although in the prototypical study of patients with ileal disease (1) the authors pointed out that the majority of the gallstones were radiopaque and therefore rich in inorganic calcium salts, so far only one group (15) has verified by analysis increased prevalence of pigment as opposed to cholesterol gallstones in Crohn's disease patients. Nonetheless, when studied both free and conjugated bilirubin levels are elevated markedly in gallbladder biles of patients with Crohn's disease (unpublished observations). Pitt and colleagues (12) on the basis of their experiments with ileal-resected prairie dogs, speculated that gallbladder stasis, hormonal changes, gallbladder mucus production and hemolysis might play a role in pigment gallstone formation, but insights into the possible pathophysiological mechanisms were not forthcoming.

Another common complication in patients with ileal dysfunction is calcium oxalate urolithiasis (17), which is caused by enteric hyperoxaluria (18). Chadwick and colleagues (18) proposed that fat malabsorption by removing calcium from solution as calcium soaps may result in enhanced intestinal oxalate absorption by increasing its levels in solution. BS and/or fatty acids as well as an intact colon appear necessary for the enteric hyperoxaluric syndrome (19,20), suggesting altered colonic mucosal permeability. Because both mono- or dicarboxylic oxalate (pKa's ($H_2O$)=1.3, 4.3 at 25°) (21) and bilirubin (proposed pka's (0.15M NaCl)≈6.8/8.1, 8.4/9.3 at 21°–25°) (22,23) have high affinities for calcium (24,25), we hypothesized that "enteric hyperbilirubia" may be the endogenous equivalent of enteric hyperoxaluria in patients with BS malabsorption. To test this hypothesis, we investigated whether ileectomy-induced BS malabsorption in the rat resulted in increased bilirubin secretion into bile. Our results are consistent with the postulate that an intestinal deconjugation, absorption, and hepatic extraction, reconjugation cycle occurs for bilirubin in ileal disease Oust as is well established in health for BS) (26), providing a putative pathophysiological mechanism for increased bilirubin conjugate levels in bile in patients with BS malabsorption.

Methods

Animals. Male Spraque-sawley rats (Charles River, Wilmington, Mass.) of body weight (B.W.) 200–300 g were studied. They were caged at 23° C. with a 12 hour daylight cycle and were fed a standard rat chow diet. All aspects of the study conformed to accepted criteria for the care and experimental use of laboratory animals, and was consistent with euthanasia recommendations of the American Veterinary Medical Association. All protocols were approved by the Harvard Medical Area Standing Committee on Animals.

Surgical procedures. Rats were fasted for 36 hours and surgery was performed under sterile conditions following pentobarbital anesthesia (35 mg per kg B.W., i.p.). Through a midline abdominal incision the small intestine was presented and was placed on hot-moistened gauzes. For ileectomy or distal jejunectomy respectively, 8 cm segments of intestine were resected 0.5 cm or 16.5 cm proximal to the ileocecal junction. Intestinal continuity was restored with end-to-end anastomoses performed with a layer of 5–0 silk sutures. Resection in the ileocecectomy group was followed by an end-to-end jejunocolonic anastomosis. For ileocolonic transposition, the ileum was mobilized and divided, leaving vascular supply and innervation intact. The ileal segment was then interposed in a transected proximal colon, 5 cm distal to the ceca-colonic junction. For proximal jejunectomy, 8 cm of small bowel was resected 2 cm distal to the ligament of Treitz and the severed ends reanastomosed. In the ileal transected group, the bowel was divided 0.5 cm proximal to the ileocecal junction and then reanastomosed. Sham operation consisted of an exploratory laparotomy with mobilization of the small bowel. By definition unoperated animals did not undergo surgery, but their bile ducts were cannulated subsequently to measure biliary bilirubin and lipid secretion rates. Body temperature (37° C.) of all animals during surgery and for 24 hours thereafter, was maintained using a heating lamp. At termination of surgery, the abdominal cavity was rinsed with warm sterile saline, and the abdominal wall closed with 3–0 silk sutures; gentamycin (7 mg per kg B.W. i.m.) was administered. Postoperatively, animals were allowed free access to water but food was withheld for the first 36 hours.

Experimental design. Stool appearance and B.W. were recorded daily post-surgery. Acute biliary washout studies followed bile duct cannulation, and were carried out first at 3 days post-surgery. Ileal resected rats were compared with sham operated animals and the following controls; unoperated, ileal transected, proximal and distal jejunectomized, ileo-colonic transpositioned and ileocecectomized animals. In different sets of ileectomized, ileocolonic transpositioned and sham operated animals, biliary washout studies were carried out at 3, 5, 8 and 11 days post-surgery. Because the jejunum plays an important role in maintaining the EHC of BS in the rat (27,28), distal as well proximal jejunectomy were performed. Furthermore, since adaptation of BS reabsorption in the remaining small intestine may restore EHC of BS to normal rapidly in the rat (29), we constructed an ileo-colonic transposition to establish permanent BS spillage into the proximal colon without fecal BS loss. Ileocecectomy was carried out to examine whether removal of the cecum which in humans is more acidic (pH5–6) than the remainder of the large bowel (30) would prevent EHC of bilirubin by removing a favorable absorption site for diacidic UCB.

Because rats are coprophagous, the possibility existed that any change in biliary BS and bilirubin secretion rates might reflect an "EHC" via the fecal-oral route. Therefore, in a subset of ileectomized as well as ileal transected animals, coprophagy was prevented throughout the experiments by employing a coarse-mesh screenfloor cage and a cerival collar of plastic 4–5 cm in width. Two days prior to abdominal surgery and after short ether anesthesia, the collar was secured circumferentionally to the cervical skin with 4 (2–0) sutures.

To establish that UCB and BS concentrations in the large intestine were consistent with the lipid secretory data during biliary washout, the cecum as well as 5 cm of proximal colon were resected in four groups of ileectomized and ileal transected animals on the 3rd post-surgery day. Cecal and proximal large bowel contents were frozen at rapidly −70° C. and stored for subsequent analysis. From the same animals, blood was obtained by needle puncture of the inferior vena cava and analyzed immediately for hemolytic indices including hematocrit, hemoglobulin level and reticulocyte count as well as total bilirubin (31).

Cannulalion of the bile duct and biliary washout. Pentobarbital anaesthesia was adminished as above. Surgery was performed in non-fasted animals under dimmed lights between 9:00 and 11:00 a.m. Following a mid-line abdominal incision, the entire small and large intestines were exposed on moist gauzes and examined grossly for macroscopic "hypertrophy". The bile duct was then cannulated with a PE-10 polyethylene catheter (I.D. 0.28 mm, O.D. 0.61 mm) and using a fraction collector bile was collected in tared tubes at 15 minutes intervals for the first half hour and at 30 min intervals for the next 1.5 hrs. All tubing and glassware was covered with aluminium foil to protect bilirubin from photodegradation. This catheter was sufficiently large to prevent acute cholestasis and sufficiently short to minimize dead space. After the biliary catheter was sutured to the abdominal wall, the abdomen was closed and animals were placed in a restraining cage. Water was supplied ad libitum and each animal's body temperature was maintained at 37° C. by means of a heat-lamp and monitored with a rectal probe. Bile samples were stored on ice in the dark under argon for less than two hours and bile volume was determined gravimetrically assuming a specific gravity of unity. During this time an aliquot was taken for analysis of bile pigments by HPLC. Samples of fresh bile were also analyzed for calcium bilirubinate precipitates or other separated phases employing direct and polarized light microscopy. Bile samples were then stored at −20° C. for later analysis of BS, phospholipid and cholesterol. Total BS and bilirubin secretion rates were calculated for washout intervals up to 2 hours by multiplying bile concentrations by volumes. Bilirubin di-/monoconjugate ratios were calculated by dividing the concentrations of bilirubin diglucuronide (BDG) plus bilirubin monoglucuronide-glucoside (BMGGl) by the bilirubin monoglucuronide (BMG) concentration. Total biliary calcium was measured in five sham-operated and five ileectomized animals with and without prevention of coprophagy. At the end of each experiment, animals were euthanized with an overdose of diethyl ether or pentobarbital.

Analytic methods. Bilirubin molecular species were separated and quantified by HPLC according to the procedures of Spivak and Yuey (32) and total BS were assayed by the 3α-hydroxysteroid dehydrogenase method (33). Biliary phospholipid were measured with Bartlett's assay (34) and biliary cholesterol by HPLC (35). Total calcium was determined by atomic absorption spectrometry. With 0.1M di-n-octylamine acetate/MeOH as an ion-pairing agent, cecal and proximal colonic bilirubins were extracted from 10–50 mg portions of thawed large intestinal contents and analysed by HPLC (36). From another portion of the samples, BS were extracted with t-butanol/water (50:50, v/v) as described by Van der Meer et al. (37) and measured enzymatically (33).

Statistical Analyses. All values are expressed as means ±SEM. For multiple comparisons of data in different animal groups, we employed a one way non-parametric test (ANOVA). Student's t-test was used for comparing bile secretory (washout) data in ileectomized and sham operated animals on 3 to 11 days post-surgery as well as for comparison of washout data of ileectomized and ileal transected animals with concomitant prevention of coprophagy.

Results

Animal weight and stool appearance. B.W. of ileal resected, proximal and distal jejunectomized, ileo-colonic transpositioned and ileocecectomized animals decreased $\leq$10% during the first 5 days post-surgery. In contrast, B.W. of sham operated and ileal transected animal increased significantly ($p<0.005$) at the 3rd postoperative day compared with ileocecectomized animals. By 8 and 11 days post-surgery, B.W. of animals were not significantly different from non-operated controls (230–440 g) and ranged from 230 to 375 g. Transient (2–3 day) diarrhea, occurred in 22 of 26 ileectomized (81%), 3 of 6 ileocecectomized (50%), 2 of 6 distal jejunectomized (33%), 2 of 12 ileal transected (17%) and 1 of 6 ileo-colonic transpositioned animals (17%). In contrast, none of the sham or unoperated animals or those with proximal jejunectomy, developed diarrhea. All animals recovered rapidly from surgery and despite self-limiting weight loss and diarrhea, were otherwise healthy throughout the experiments.

Intestinal adaptation. As reported by others on the basis of histological criteria (38), hypertrophy of the residual intestine followed distal small bowel resection in the rat and was evidenced on the 3rd post-surgery day. Both ileectomy as well as distal jejunectomy resulted in hypertrophy of remaining distal small bowel and cecum (39). Ileocecectomized animals developed hypertrophy of the distal small bowel as well as the proximal colon. Hypertrophy of the distal small bowel followed proximal jejunectomy as noted in earlier studies (40,41). In animals with ileo-colonic transpositions, intestinal hypertrophy was confined mainly to the proximal colon and transposed ileum. As expected, sham operated animals did not develop intestinal hypertrophy, but ileal transected animals developed modest bowel enlargement in the vicinity of the anastomosis without evident obstruction.

Biliary lipid, bilirubin and calcium secretion rates. FIG. 1 displays representative HPLC profiles of bilirubins in rat bile at 3 days post-surgery during the earliest (0–15 min) washout period. FIG. 1A shows a chromatogram for bile of a sham operated animal which contained almost equimolar amounts of BDG, and the two isomers of BMG, whereas BMGGl concentration (peak No.3) was less than 3% of total. FIG. 1B, and C show chromatograms for bilirubins in biles of ileectomized animals, and two distinct patterns were observed. In FIG. 1B, biliary BDG was elevated while BMG levels were unchanged and in FIG. 1C, BDG levels were relatively low and BMG plus BMGGl levels were elevated. FIG. 1D displays the chromatogram for bilirubins in bile of a distal jejunectomized animal showing a pattern similar to that in FIG. 1C, except that BMGG1 levels were less elevated. In all biliary chromatograms, UCB levels (peak No 5) were either non-existent or <1% of total.

FIG. 2A plots mean (±SEM) total bilirubin secretion rates in rat bile during 0–30 min biliary washout performed at 3 days post-surgery. Bilirubin secretion rates were increased significantly (p<0.00) following ileectomy, distal jejunectomy, ileo-colonic transposition and ileocecectomy compared with proximal jejunectomized, unoperated, sham and ileal transected controls. FIG. 2B shows mean di-/monoconjugated ratios of bilirubins in bile for the same animals at 3 days post-surgery. The ratio of bilirubin conjugates increased significantly (p=0.001) following distal jejunectomy compared with proximal jejunectomized and unoperated animals. Although bilirubin di-/monoconjugate ratios (FIG. 2B) in washout bile were increased following ileectomy, ileo-colonic transposition and ileocecectomy compared to controls, they failed to reach statistical significance. FIG. 2C displays that total BS secretion rate (0–30 min) on the 3rd post-surgery day increased significantly (p=0.005) following ileectomy compared with sham operated animals; with other groups giving intermediate values. Although not statistically significant, total BS secretion rate was decreased approximately 50% in sham operated control compared with ileal transected and unoperated animals (FIG. 2C). Biliary phospholipid and cholesterol secretion rates during the acute biliary washout paralleled the findings in FIG. 2C, with significant decreases in sham operated animals compared with ileectomized and ileal transected animals 1.0±0.2 versus 2.2±0.3 and 2.2±0.2 $\mu$mol/h/100 g respectively, for phospholipid (p<0.001) and 0.11±0.01 versus 0.22±0.05 and 0.17±0.02 $\mu$mol/h/100 g respectively for cholesterol (p<0.01). Biliary calcium secretion rates were not significantly different in ileectomized or sham operated animals (3.0±0.4 versus 2.6±0.3 $\mu$mol/h/100 g) respectively.

Table 1 summarizes total bilirubin secretion rates at 30 min intervals during biliary washout in all groups of rats at 3 days post-surgery. In the earliest time period, bile pigment secretion rate was increased significantly in animals with distal small bowel resections including ileo-colonic transposition. However, during 30–60 and 60–90 min of biliary washout, total bilirubin secretion rates decreased in all animal groups and comparisons between experimental and control groups became less significant or were not different. Nonetheless, by 90–120 min of washout, bilirubin secretion rates ileocolonic transposed and ileectomized rats remained elevated and were identical to those during the acute phase (0–30 min) of the biliary wash-out (Table 1).

Total biliary BS secretion rates are listed in Table 2. As expected all were maximal during 0–30 min of washout, and then over the subsequent time intervals decreased progressively reaching significantly low values at 90–120 mins (p<0.05) in unoperated, sham, ileal transected and ileocolonic transpositioned animals compared with initial levels. This well known depletion of the BS pool is reflected in diminution of BS secretion and was associated with an expected decrease in bile flow. By 90–120 min of pool washout, biliary BS secretion rates were 40–70% of initial (0–30 min) levels, indicating complete interruption of the EHC.

Figure 3:
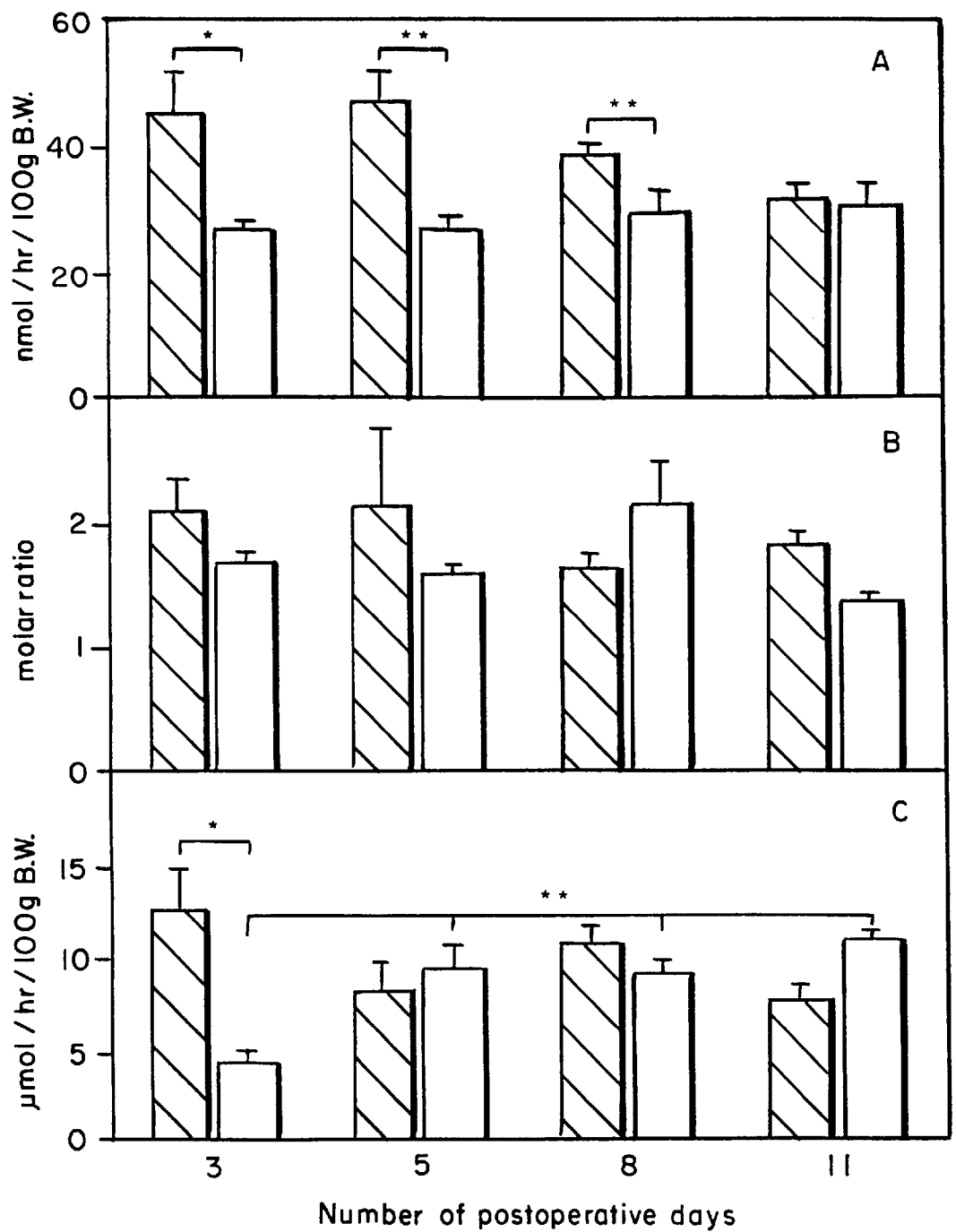
FIG. 3. Secretion of total bilirubin and BS during 0–120 min of biliary washout in ileectomized and sham operated animals as functions of number of days following surgery. (A) Total bilirubin secretion rate (nmol/hr/100 g B.W.); (B) Bilirubin di-/monoconjugate ratio; c) Total bile salt secretion rate ($\mu$mol/hr/100 g B.W.). Dark bars represent ileectomized and open bars sham-operated animals. Asterisks indicate statistically significant differences between groups: *$p<0.005$, **$p<0.05$ as indicated by the serifs and bracket ends: Data are expressed as means±S.E.M.

BS and bilirubin secretion rates during biliary washout as functions of days post-surgery. FIG. 3(A–C) summarizes bilirubin and bile salt secretion rates over 0–120 min of biliary wash-out in ileectomized and sham-operated animals as functions of the number of days post-surgery. FIG. 3A demonstrates that following ileectomy, total bilirubin secretion rate declined progressively from a high level at 3 days to reach that of the sham operated animals by the 11th postoperative day. Total bilirubin secretion rate was not only significantly smaller in sham operated animals (FIG. 3A), but remained constant from 3 to 11 days post-surgery. FIG. 3B demonstrates that the bilirubin di-/monoconjugate ratios were variable and were not statistically different from sham operated animals over the entire 11 day period. In ileectomized animals, total BS secretion rates (FIG. 3C) were significantly elevated on the 3rd post-surgical day, and thereafter decreased, remaining constant and equivalent to those of the sham operated animals from 5 to 11 days. In sham operated animals, total BS secretion rats were significantly lower at 3 compared with 5 to 11 days post-surgery (FIG. 3C). In ileo-colonic transpositioned animals (data not shown), total BS secretion rates from 3 to 11 days post-surgery displayed the same behavior as in ileectomized animals (FIG. 3C).

Figure 4:
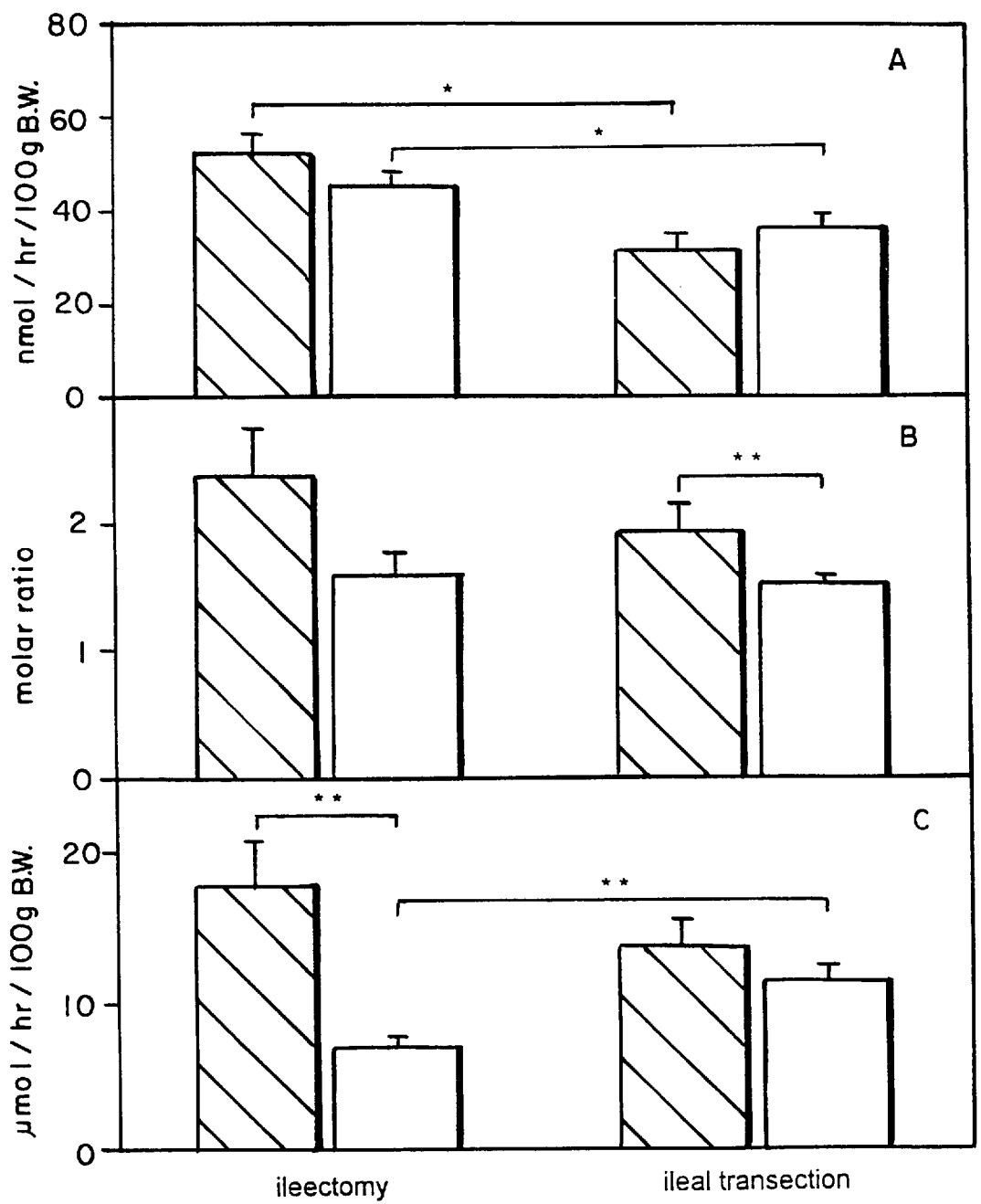
FIG. 4: Biliary bilirubin and BS secretion rates during 0–30 min biliary washout, 3 days following ileectomy and ileal transection in rats with and without prevention of coprophagy. Shaded bars represent rats capable of coprophagizing and open bars represent rats in which coprophagy was prevented. (A) Total bilirubin secretion rate (nmol/hr/100 g B.W.); (B) Bilirubin di-/monoconjugate ratios; c) Total bile salt secretion rate ($\mu$mol/hr/100 g B.W.). Asterisks indicate statistically significant differences between groups: *$p \leq 0.005$; **$p<0.05$ as indicated by the ends of the brackets.

Influence of coprophagy on biliary secretion rates of bile salt, bilirubin and calcium. FIG. 4 displays the dramatic effects of coprophagy prevention on biliary bilirubin and BS secretion rates at 3 days post-surgery in ileectomized and ileal transected animals. FIG. 4A shows that total bilirubin secretion rates were significantly (p≤0.005) elevated following ileectomy compared with ileal transected animals (see FIG. 2), and that prevention of coprophagy (open bars) did not appreciably influence these values. In contrast with prevention of coprophagy, mean bilirubin di-/monoconjugate ratios decreased in both groups of animals (FIG. 4B) which reached statistical significance (p<0.05) in ileal transected animals. This was principally due to BMGG1 levels which were elevated in bile in the coprophagous state (FIG. 1C) and diminished comparable to those in control animals following prevention of coprophagy (FIG. 1A). Furthermore, total BS secretion rates in ileectomized animals decreased markedly (p<0.01) with prevention of coprophagy (FIG. 4C), and biliary outputs were significantly lower (p<0.05) than in ileal transected animals. This finding indicates that fecal-oral ingestion of BS in coprophagous animals contributes significantly to "EHC" of BS in the ileectomized state. Prevention of coprophagy in ileectomized animals did not influence biliary calcium secretion rates which decreased non-significantly from 3.0±0.4 to 2.6±0.1 $\mu$mol/h/100 g B.W.

Serum hemogram analyses. In blood drawn at 3 days post-surgery, hemoglobin (13.5±0.8 vs 14.1±0.9 g/dl), hematocrit (41.9±1.9 vs 43.6±2.5%) and reticulocyte count (2.7±0.4 vs 2.6±0.4) were not statistically (p>0.6) different in ileectomized (n=4) compared with ileal transected (n=3) animals, respectively. Furthermore, plasma total bilirubin levels (31) were below the detectable limit (0.1 mg/dl) in both sham as well as ileectomized animals (n=2).

Cecal and proximal colonic bilirubin and bile salts concentrations. Table 3 lists large intestinal BS and UCB concentrations at 3 days following ileectomy and ileal transection surgery (n=4 each). Concentrations of UCB and BS in the cecum plus proximal colon were increased by 5- and 8-fold, respectively in ileectomized, compared with ileal transected rats. Since biliary bilirubin outputs were most elevated on the 3rd postoperative day (Table 1) it is likely that these intraluminal levels approximated maximal values.

Direct and polarizing light microscopy. Neither calcium bilirubinate precipitates nor cholesterol monohydrate crystals were observed in bile of ileectomized or sham operated animals (n=17) at 3 days post-surgery, indicating that biles remained unsaturated and isotropic.

Discussion

The most important findings in this study was that distal small bowel resection in the rat resulted in a 2 fold increase in total bilirubin secreted into bile, whereas proximal small bowel resection, sham operation or ileal transection did not have this effect. Because of the use of appropriate controls, we can infer that hypersecretion of bilirubin into bile is unlikely to have originated in increased red-cell destruction, increased ineffective erythropoiesis or increased bilirubin production from non-hemoglobin sources (FIG. 3). By exclusion this strongly suggests that an induced EHC of bilirubin from BS malabsorption accounts for the principal results. Bilirubin secretion rates were elevated most markedly during the first 30 min of cannulation, when the EHC of BS was closest to being intact (7,42) at least for the ileectomized state, and at a time when biliary BS secretion rates are known to be relatively unaffected by mechanical EHC interruption in the rat (43). Because in the ileectomized animals EHC of bilirubin is apparently a consequence of a surgically-induced interruption of the EHC of BS, then with continuous biliary washout, the BS pool became depleted and a continuous decreases in both BS and bilirubin secretion rates resulted. This is most likely related to depletion of intraluminal BS concentrations in the large intestine which would impair solubilization and absorption of UCB.

Because UCB in bile was less than 1% of total bilirubin, it was not expected that the solubility product of the acid (or less likely neutral) salt of calcium and UCB would be exceeded (25). Accordingly, we did not observe calcium bilirubinate precipitates in any hepatic bile. This is in agreement with observations of Pitt and colleagues (12), that calcium levels were normal in hepatic bile of ileectomized prairie dogs. However, gallbladder bile analysis from the same animals revealed increased calcium levels, suggesting that increased calcium influx into bile takes place in the gallbladder possibly as a result of elevated bilirubin conjugate levels which appear to bind calcium as soluble complexes (44).

Figure 2:
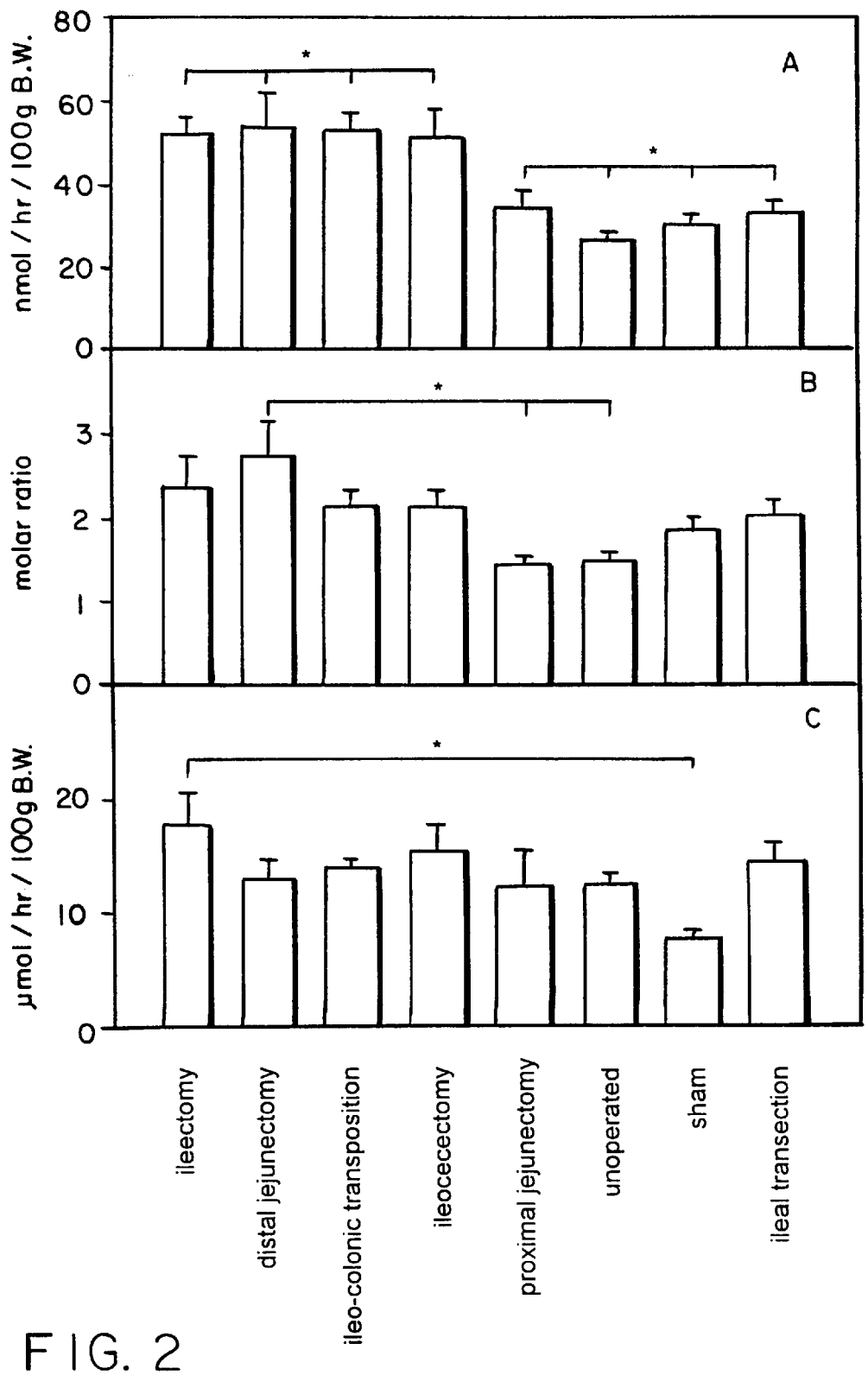
FIG. 2: Secretion rates of bilirubin and bile salts (BS) during 0–30 min of biliary washout performed 3 days following surgery collection in all animal groups (n=5–9 in each). (A) Total bilirubin secretion rate (nmol/hr/100 g B.W.); (B) Bilirubin di-/monoconjugate ratio; c) Total bile salt secretion rate ($\mu$mol/hr/100 g B.W.). Asterisks indicate statistically significant differences ($p<0.005$) between perpendicular serifs within and at ends of the square brackets. Data are expressed as means±S.E.M.

Previous studies have reported that an increased bilirubin load reaching the parenchymal cells of the liver from any source will increase the bilirubin di-/mono conjugate ratio in bile (45). We have no precise explanation for our observation that following distal small bowel resection relatively more bilirubin diconjugates that monoconjugates augmented by BMGGl were secreted into bile (FIGs. 1 and 2). It is possible that the changing patterns of BS fluxes through the hepatocyte could affect the affinity of bilirubin UDP-glucuronyltransferases for glucose compared with glucuronic acid (46,47). This belief is supported by the fact that prevention of coprophagy in ileectomized animals resulted in a decrease in total BS secretion rate into bile from inhibition of the fecal-oral "EHC" and concomitantly normal biliary BMGGl levels resulted (see results).

It is well known, that distal small bowel resection in the rat induces hypertrophic changes in the residual intestine as early as the 3rd post-operative day (38). Concomitantly, compensatory BS reabsorption in the proximal small intestine restores the EHC to normal (29). This is consistent with our observations that transient weight loss was less than 10% of initial B.W. and full recovery was achieved by the 5th post-surgical day. Diarrhea disappeared in all animals within 2–3 days, and bilirubin hypersecretion was abolished at 11th post-surgical day (FIG. 3). It is logical to assume that intestinal absorption of bilirubin occurred at this time because no further BS malabsorption took place. Although intestinal hypertrophy in ileo-colonic transpositioned animals was confined mainly to the proximal large intestine, biliary secretion rates of bilirubin were elevated only slightly in these compared with ileectomized animals, indicating that compensatory BS reabsorption still occurred in the proximal small bowel. Therefore in the rat, an animal with a remarkable capacity for intestinal adaptation, the time-frame for observing the effect of ileectomy and BS malabsorption on intestinal handling of bilirubin was confined to less than 1 week post-surgery.

Interestingly, ileectomy resulted in marked increases rather than an anticipated decrease in total BS secretion rate (FIG. 4). It is known that it requires 2 to 3 days of biliary diversion, to upregulate de novo BS synthesis to compensate for chronic BS loss in the rat (42). Because coprophagy may contribute 40% of nutritional requirements in the healthy rat (48), we anticipated that fecal-oral ingestion of BS in animals with BS malabsorption and diarrhea could contribute significantly to "EHC" of BS as proven in the rabbit (49). This was confirmed by our observations in ileectomized animals (FIG. 4) that effective prevention of coprophagy reduced biliary BS secretion rates dramatically. Although coprophagy resulted in a considerable EHC of BS with more BS available for reabsorption of UCB, total bilirubin secretion rates were not appreciably altered in the non-coprophagic animals (FIG. 4), suggesting insolubility or degradation of bilirubin (50,51) in either the feces or after ingestion in the small intestine.

It was curious that sham operation resulted in a non-significant reduction in biliary BS secretion compared with all other animal groups and was significantly different from the ileectomy group (FIG. 2). However, bilirubin secretion rates and conjugate ratios in sham operated animals were not different from unoperated animals or ileal transected controls. The depressed biliary BS secretion rate is in accordance with similar observations in rhesus monkeys during early postoperative periods (52). However, in contrast to the rhesus monkey, BS secretion rate in the rat was restored to normal at 5 days post-surgery (FIG. 3). Clearly coprophagy could not contribute to an elevation the "low" BS secretion in sham animals since it was the only group that showed no diarrhea post-surgery. In ileal transected animals, biliary BS secretion rates were higher than in sham (FIG. 2), most likely because of diarrhea which occurred in 17% of animals and early "adaptive" responses as a result of intestinal transection (53).

In animals with healthy livers, biliary secretion of bilirubin is determined by the hepatic flux of UCB, which is increased by ineffective erythropoiesis, increased red cell destruction (hemolysis), or increased heme-destruction from non-hemoglobin sources (54). While all of these are very unlikely causes for our observations, we show below that intestinal reabsorption of UCB (55) was clearly to be most probable cause. In the current study, no animal developed appreciable or prolonged postoperative bleeding, rats were healthy and not infected throughout the experimental periods and in ileal transected and resected animals serum analyses did not reveal hemolysis (see results). There is no a priori reason (see 54) why ineffective erythropoiesis, or increased red cell destruction in the absence of bleeding and increased heme enzyme catabolism from non-hemoglobin sources, could be induced by small bowel surgery. Furthermore, control procedures including proximal jejunectomy and ileal transection (Table 1, FIG. 2) both of which involved extensive surgery and operation times, did not increase bilirubin secretion rates into bile. This indicated that increased bilirubin secretion rates were unrelated to intestinal resectionper se. This is a persuasive factor in this work that should rule-out an induced hemolytic disorder or ineffective erythropoesis, is that with progressive small bowel adaptation, hypersecretion of bilirubin was progressively curtailed and was eliminated at 11 days post-surgery (FIG. 3). One might argue that possible differences between the experimental groups were related to the use of anesthesia. However, it has been shown by Gourley and colleagues (56) that pentobarbital anesthesia which was used sparingly in this work, does not influence hepatic bilirubin conjugation or biliary secretion rate appreciably in the rat. Therefore, in light of these considerations, and the otherwise healthy state of all animals it is reasonable to conclude that increased bilirubin secretion rates following distal small bowel resection in the rat was a result of BS malabsorption inducing an EHC of bilirubin.

It is reported that first pass extraction of unconjugated bilirubin is constant i.e. independent of load (57), then when there is increased input from the intestine, there would be increased unconjugated bilirubin in plasma. Nevertheless, this anticipation was not fulfilled since the rat model is restrictive in that bilirubin is virtually undetectable in normal rat plasma (58) and in both our sham and ileectomized rats the plasma total bilirubin levels (see results) were below the detectable limit of ≈0.1 mg/dl (31).

Lester and Schmid (59,60) demonstrated that UCB in contrast to its conjugates can be absorbed passively from intestinal mucosa of rats and humans. In the case of bilirubin conjugates this cannot occur since the intact molecules are too large and polar (60). Following absorption from the intestine and return to the liver, approximately 20–30% of bilirubin is cleared from portal blood by the healthy rat liver in a single pass (57,61) and subsequently highly efficiently conjugated and resecreted into bile (46,47). The discrepancy between the 5 to 8 fold increase in cecal bilirubin (Table 3) and the most a 2 fold increase in biliary bilirubin concentration and output (FIG. 2), could be explained by binding of UCB to undigested residue and bacteria in colonic contents (50,55), binding to BS monomers and micelles (22) and juxtamucal unstirred water layers acting as diffusion barriers (62). An EHC of bilirubin is normally not evident in health (60); so that bilirubin secretion into bile does not exceed bilirubin production (63). In mammals, virtually all bilirubin molecules are conjugated with one or two glucoside molecules by the liver (47), thus the size and charge of the molecules prevents their intestinal reabsorption (59,60). Second, after bilirubin conjugates are hydrolyzed spontaneously or by bacterial β-glucuronidases in the distal small bowel (64), UCB precipitates as an insoluble calcium salt (51) or is further converted by bacterial catabolism into urobilinogens (50,64). Subsequently urobilinogens may be absorbed in part from the intestine (65) to undergo limited enterohepatic cycling (66). Therefore, as strongly indicated by the studies herein, intestinal reabsorption of bilirubin can only occur if (a) bilirubin is deconjugated rapidly, (b) bacterial degradation is slow or prevented, (c) UCB remains in solution, (d) complexing with $Ca^{2+}$ does not occur.

The solubility of UCB in model bile or upper small intestinal luminal systems depends upon pH and BS concentration (22,67). Since at least in humans, the pH of the large intestine is below 7 (30), bilirubin is present predominantly as the diacid that is only sparingly soluble (22,23) but becomes partially ionized in the presence of BS (22). By binding to BS monomers and micelles, the aqueous solubility of UCB increases (67,68). As we have shown here, total BS levels in the proximal large intestine were increased eight-fold following ileectomy compared with ileal transected animals (Table 3) and furthermore almost all animals developed diarrhea, indicative of increased BS spillage into the colon (69).

The UCB level in the proximal large intestine was increased five-fold (Table 3) in ileectomized animals compared with ileal transected animals. With an BS/UCB molar ratio of approximately 500:1 (Table 3), UCB should be solubilized and precipitation prevented (67,68). The rate of UCB absorption should be related directly to its monomeric activity. Micellar solublization may actually decrease intestinal absorption for a given total aqueous concentration of an insoluble solute (70). Because UCB can be absorbed from the intestine by passive nonionic diffusion (59) and the rate of UCB absorption will depend on the amount of UCB solubilized, it seems reasonable to assume that increased levels of solublized UCB following ileectomy resulted in sustained intestinal reabsorption. This concept is supported by the observation that intraduodenal infusion of UCB to rats when "solubilized" by a high concentration of sodium dehydrocholate a non-micelle forming synthetic BS, resulted in bilirubin absorption from the gut, whereas administration of bilirubin alone did not have this effect (71).

Perfusion of the rat colon with BS and fatty acids is known to increase intestinal permeability to oxalate (19) and it is considered that this tiny di-anion is hyperabsorbed in the presence of BS possibly because the tight junctions of the colon become sufficiently large so as to admit a molecule of its size. It is unlikely that the same could hold true for a molecule as large as bilirubin, so it appears that the solubilizing role of BS for diacidic UCB as well as the latter's ability to penetrate membranes (59) are the most important factors promoting absorption (67). Because total bilirubin secretion rate following ileocecectomy in the rat became elevated significantly (FIG. 2), and was of the same order of magnitude as in ileectomized and ileo-colonic transpositioned animals (FIG. 2), this suggested that intestinal reabsorption of bilirubin can take place from the proximal colon as well as the cecum.

It is necessary to consider whether intestinal reabsorption of UCB could have occurred from the small intestine. As pointed out in recent work (72), extensive deconjugation of BS does occur in the small intestine of the rat, but taurine conjugates which are the predominant species in rats are relatively resistant. Even though the ileocecal valve was left intact in our rats at surgery, some bacterial overgrowth in the rat's small intestine is likely since the animal is coprophagous. Nevertheless, since bile salt deconjugation occurs for the same reasons as bilirubin deconjugation in this setting, and this would negate the solublizing effect of BS on UCB in the remaining small intestine since the deconjugated BS would either precipitate or be absorbed rapidly (73). An issue that needs to be addressed in future studies is whether an increased colonic BS by high affinity binding of UCB may inhibit formation of urobilinogens by either their antibiotic effect on the anerobic flora or by preventing UCB diffusing into bacterial cells (67).

Pathophysiological implications. Several abnormalities in patients with Crohn's disease speak in favour of an induced EHC of bilirubin since their gallbladder biles have significantly increased levels of bilirubin conjugates and UCB (unpublished observations). Ileal dysfunction in these patients may lead to excessive BS loss and cholerrheic diarrhea may persist for long periods or indefinitely (69). Nevertheless, increased exposure of BS to intestinal bacteria may convert chenodeoxycholate into ursodeoxycholate rapidly (74) and thus prevent BS catharsis. We speculate that BS malabsorption from any cause may lead to induced EHC of bilirubin and either hyperbilirubilia or hyperbilirubinemia depending on the health and maturity of the liver with respect to UCB uptake, conjugation and secretory status.

The present work can be related to human stone disease which is seen with increased frequency in Crohn's disease patients and is pigment in type. The question arises as to whether a doubling in biliary bilirubin secretion rate could provide sufficient substrate in the gallbladder for supersaturation with calcium bilirubinate. In the congenitally hemolytic mouse of genotype nb/nb, total bilirubin secretion rates increase ten to twenty fold over wild strains and prevalence of pigment gallstones is 75% (76,77). In humans with inherited hemolytic anemias (78,79), 10 fold elevations of biliary bilirubin levels are not uncommon. Nonetheless, after ileal resection in the prairie dog, Pitt and colleagues (12) found a prevalence of pigment gallstones of 44% at 4 weeks and yet at that time total bilirubin levels in hepatic bile were only twice that of sham-operated controls, a level identical to those observed in our rats following ileectomy (Table 1, FIG. 2). Clearly in animals with gallbladders, residence time, endogenous β-glucuronidase activity and ionized calcium levels play crucial interdependent roles in elevating the ion-products of calcium bilirubinate salts above the equilibrium solubility limits (80). It is also noteworthy in this connection, that mild chronic or episodic hemolysis in humans can lead to increased pigment gallstone formation such as occurs with malaria, prosthetic heart values, and alcoholic cirrhosis (80).

In conclusion, we have demonstrated that distal small bowel resection in the rat results in a doubling of conjugated bilirubin secretion rates into bile. We argue herein that this is caused by an EHC of bilirubin in ileectomized animals as a result of an interrupted EHC of BS with BS malabsorption small bowel. Assuming that the same pathobiology is operative in humans, this would imply that "enteric hyperbilirubilia" might be the endogenous equivalent of enteric hyperoxaluria in BS malabsorption syndromes.

References for Example 1
1. Heaton, K. W., et al., Brit Med J 1969;3:494–496.
2. Baker, A. L., et al., Digestive Dis 1974;19:109–112.
3. Buchwald, H., et al., N Engl Med J 1990;323:946–955.
4. Dowling, R. H., et al., Gut 1972;13:415–420.
5. Marks, J. W., et al, Am J Dig Dis 1977;22:1097–1100.
6. Mok, H. Y. I., et al, Dig Dis Sci 1978;23:1067–1075.
7. Dowling, R. H., et al., J. Clin. Invest. 1971;50:1917–1926.
8. Férézou, J., et al., Gastroenterology 1993;104:1786–1795.
9. Lapidus, A., et al., Gut 1991;32:1488–1491.
10. Åkerlund, J., et al., Gut 1994;35:1116–1120.
11. Bickerstaff, K. I., et al., Am J Surg 1983;145:34–40.
12. Pitt, H. A., et al., Surgery 1984;96:154–162.
13. Nilsson, L. O., et al., J Surg Res 1984;7:304–308.
14. Coyle, J. J., et al., Surg Forum 1980;31:139–141.
15. Magnuson, T. H., et al., Arch Surg 1989;124:1195–1200.
16. Dawes, L. G., et al., Surg Forum 1991;42:188–189.
17. Dowling, R. H., Lancet 1971;1103–1106.
18. Chadwick, V. S., et al., N Engl J Med 1973;289:172–176.
19. Dobbins, J. W., et al., Gastroenterology 1976;70:1096–1100.
20. Dobbins, J. W., et al., N Engl Med J 1977;296:298–301.
21. Albert, A., and Sergeant, The determination of ionization constants, 2nd ed. London Chapman and Hall 1971:p. 89.
22. Ostrow, J. D., et al., J Lipid Res 1988;29:335–348.
23. Hahm, J. S., et al., J Lipid Res 1992;33:1123–1137.
24. Earnest, D. L., et al., Trans Assoc Am Physicians 1975;88:224–234.
25. Ostrow, J. D., et al., Hepatology 1984;4:38S–45S.
26. Carey, M. C., and Duane, W. C., In: Arias, I. M., et al., eds. The Liver: Biology and Pathology, 3rd ed. New York: Raven Press, 1994:714–767.
27. McClintock, C., et al., Am J Physiol 1983;244:G507–G514.
28. Mok, H. Y. I., et al., Gut 1974; 15:247–253.
29. Tilson, M. D., et al., Surgery 1975;77:231–234.
30. Evans, D. F., et al., Gut 1988;29:1035–1041.
31. Doumas, B. T., et al., Clin Chem 1985;31:1779–1789.
32. Spivak, W., et al., Biochem J 1986;234:101–109.
33. Turley, S. D., et al., J Lipid Res 1978;19:924–928.
34. Bartlett, G. R., J Biol Chem 1959;234:466–468.
35. Vercaems, R., et al., J Chromatogr 1989;494:43–52.
36. McDonagh, A. F., et al., J Am Chem Soc 1982;104:6865–6867.
37. Van der Meer, R., et al., t-Butanol extraction of faeces: a rapid procedure for enzymatic determination of fecal bile acids. In: Beynen, A. C., et al., eds. Cholesterol metabolism in health and disease. Ponsen & Looyen, Wageningen. 1985:113–119.
38. Hanson, W. R., et al., Gastroenterology 1977;72:701–705.
39. Perry, P. M., Ann Royal Coll Surg Engl 1975;57:139–147.
40. Scarpello, J. H. B., et al., Clin Sci Mol Med 1978;54:241–249.
41. Dowling, R. H., Booth, C. C., Clin Sci 1967;32:139–149.
42. Eriksson, S., Proc Soc Exp Biol Med 1957;94:578–582.
43. Smit, M. J., Biochem. J. 1990;269:781–788.
44. Ostrow, J. D., Murphy, N. H., Biochem J 1970;120:311–327.
45. Fevery, J., et al., Hepatology 1983;3:177–183.
46. Hauser, S. C., and Gollan, J. L., Hepatic UDP-glucuronyltransferase and the conjugation of bilirubin. In: Ostrow, J. D., ed., Bile Pigments and Jaundice, Molecular Metabolic and Medical Aspects, New York: Marcel Dekker, 1986:211–241.
47. Chowdhury, J. R., Chowdhury, N. R., Sem Liver Dis 1983;3:11–23.
48. Fajardo G, Hömicke, H., Brit J Nutrition 1989;62:551–561.
49. Yahiro, K., et al., Gastroenterol Jpn 1979;14:545–552.
50. Watson, C. J., et al., Proc Soc Exp Biol Med 1958;98:707–711.
51. Ostrow, J. D., Celic, J., Hepatology 1987(abst).
52. Herman, A. H., et al., Surg Forum 1971;22:378–380.
53. Loran, M. R., Althausen, T. L., Am J Physiol 1958;193:516–520.
54. Berlin, N. I., Overproduction of bilirubin. In: Ostrow, J. D., ed. Bile Pigments and Jaundice, Molecular and Medical Aspects, New York: Marcel Dekker, 1986:271–277.
55. Lester, R., Troxler, R. F., Gastroenterology 1969;56:143–169.
56. Gourley, G. R., et al., Hepatology 1985;5:610–614.
57. Bloomer, J. R., Zaccaria, J., Am J Physiol 1976;230:736–742.
58. With, T. K., Bile Pigments of blood. In: Bile Pigments. New York. Academic Press, 1968.
59. Lester, R., Schmid, R., J Clin Invest 1963;42:736–746.
60. Lester, R., Schmid R., N Engl Med J 1963;269:178–182.
61. Wolkoff, A. W., et al., J Clin Invest 1978;61:142–149.
62. Levitt, M. D., et al., J Clin Invest 1990;86:1540–1547.
63. Berk, P. D., et al., J Clin Invest 1969;48:2176–2189.
64. Saxerholt, H., et al., Scand J Clin Lab Invest 1986;46:341–344.
65. Billing, B. H., Intestinal and renal metabolism of bilirubin including enterohepatic cycling. In: Ostrow, J. D., ed. Bile Pigments and Jaundice, Molecular and Medical Aspects, New York: Marcel Dekker,. 1986;255–269.

66. Lester, R., Schmid, R., J Clin Invest 1965;44:722–730.
67. Ostrow, J. D., et al., J Lipid Res 1994;35:1715–1737.
68. Carey, M. C. and W. Spivak, Physical Chemistry of bile pigments and porphyrins with particular reference to bile. In: Ostrow, J. D., ed. Bile Pigments and Jaundice, Molecular and Medical Aspects, New York: Marcel Dekker, 1986;81–132.
69. Hofmann, A. F., Poley, J. R., Gastroenterology 1972;62:918–934.
70. Carey, M. C., Hernell, O., Sem Gastrointest Dis 1992;3:189–208.
71. Lücking, T., Künzer, W., Klin. Wochenschr. 1967;15:547–648.
72. Zhang, R., et al., Am J Physiol 1992;262G351–G358.
73. Toskes, P. P., Donaldson, R. M. Jr., Enteric bacterial Flora and bacterial overgrowth syndrome, In: Sleisenger, M. H., et al., eds. Gastrointestinal Disease. Volume II. 5th edition Philadelphia: W. B. Saunders Co 2(5) 1993;1106–1118.
74. Miwa, H., et al., Gastroenterology 1986;90:718–723.
75. Trotman, B. W., et al., J Clin Invest 1980;65:1301–1308.
76. Trotman, B. W., et al., Gastroenterology 1983;84:719–724.
77. Schull, S. D., et al., Gastroenterology 1977;72:625–629.
78. Fevery, J., et al., Eur J Clin Invest 1980;10:219–226.
79. Cahalane, M. J., et al., Sem Liver Dis 1988;8:317–328.
80. Apstein, M. D., Carey, M. C., Gallstones. In: Branch, W. T. Jr. ed. Office Practice of Medicin. 3rd ed. Philadelphia: W. B. Saudners Co. 1994;277–295.

TABLE 1

Total bilirubin secretion rates in rats during biliary washout performed at 3 days post-surgery.

| Operative group[b] | (N)[c] | Total bilirubin secretion rate (nmol/hr/100 g B.W.)[a] | | | |
|---|---|---|---|---|---|
| | | 0–30 min[d] | 30–60 min | 60–90 min | 90–120 min |
| Unoperated | (6) | 23.4 ± 1.9[e] | 19.5 ± 1.3 | 18.0 ± 1.9 | 23.1 ± 1.8 |
| Sham | (9) | 26.8 ± 2.5 | 24.6 ± 1.6 | 25.1 ± 1.2 | 29.3 ± 1.7 |
| Ileal transection | (6) | 29.4 ± 3.0 | 27.0 ± 1.7 | 22.4 ± 2.0 | 25.6 ± 5.3 |
| Proximal jejunectomy | (6) | 32.3 ± 3.7 | 34.7 ± 3.7 | 33.6 ± 5.6 | 39.4 ± 7.9 |
| Distal jejunectomy | (6) | 53.1 ± 8.0*‡§¶f | 43.2 ± 4.1§ | 41.2 ± 3.2§ | 43.8 ± 4.5 |
| Ileo-colonic transposition | (5) | 51.5 ± 4.8*‡§¶ | 46.5 ± 4.3*§ | 37.2 ± 3.4§ | 51.7 ± 5.1*‡§ |
| Ileocecectomy | (6) | 49.7 ± 6.8*‡§¶ | 34.8 ± 3.6 | 34.1 ± 5.2 | 36.8 ± 3.8 |
| Ileectomy | (8) | 52.2 ± 3.7*‡§¶ | 45.1 ± 6.3§ | 47.4 ± 7.5*‡§ | 53.7 ± 7.5*‡§ |

[a]Total bilirubin in bile was measured by HPLC (32)
[b]Surgical preparation of rats
[c]N = number of animals in group.
[d]Timing of biliary washout from moment of cannulation of bile duct.
[e]Represent mean ± SEM.
[f]Superscripts indicate statistically significant differences ($p < 0.001$) compared with
*sham;
‡ ileal transected;
§ unoperated;
¶ proximal jejunectomized animals

TABLE 2

Total bile salt secretion rates in rats during biliary washout performed 3 days post-surgery.

| Operative group[b] | (N)[c] | Total bile salt secretion rate (μmol/hr/100 g B.W.)[a] | | | |
|---|---|---|---|---|---|
| | | 0–30 min[d] | 30–60 min | 60–90 min | 90–120 min |
| Unoperated | (6) | 11.3 ± 0.8[e] | 7.0 ± 0.8 | 5.6 ± 0.5 | 5.6 ± 0.9 |
| Sham | (9) | 6.3 ± 1.0 | 4.2 ± 0.7 | 3.1 ± 0.5 | 3.6 ± 0.6 |
| Ileal transection | (6) | 13.0 ± 1.7 | 9.3 ± 2.1 | 5.9 ± 1.0 | 5.5 ± 0.9 |
| Proximal jejunectomy | (6) | 11.4 ± 3.0 | 8.4 ± 1.5 | 6.5 ± 1.4 | 7.5 ± 2.1 |
| Distal jejunectomy | (6) | 12.6 ± 1.8 | 13.4 ± 3.7*f | 12.1 ± 4.7 | 8.9 ± 1.7 |
| Ileo-colonic transposition | (5) | 13.3 ± 0.7 | 10.6 ± 0.8 | 8.2 ± 1.0* | 9.9 ± 0.8* |
| Ileocecectomy | (6) | 14.5 ± 2.3 | 9.7 ± 1.5 | 9.3 ± 1.2* | 8.7 ± 1.4 |
| Ileectomy | (8) | 17.7 ± 2.8* | 12.7 ± 2.5* | 9.8 ± 1.7* | 10.3 ± 1.7* |

[a]Total bile salts were measured by an enzymatic method (33).
[b]Surgical preparation of rats.
[c]N = number of animals in each group.
[d]Time interval of biliary washout from moment of cannulation of bile duct
[e]Represents mean ± SEM.
[f]Asterisks indicate statistically significant differences ($p < 0.05$) between resected and/or transpositioned versus sham operated animals

TABLE 3

Cecal plus proximal large intestinal bilirubin and bile salt concentrations in ileectomized and ileal transected rats

|  | ileectomy (n = 4) | ileal transection (n = 4) |
|---|---|---|
| UCB (nmoles/g dry intestinal content)[a] | 70.4 ± 32.3*[b] | 14.1 ± 2.9 |
| Total BS (μmoles/g dry intestinal content)[a] | 35.7 ± 6.7‡[c] | 4.7 ± 1.7 |

[a]Measured as described in Methods at 3 days post-surgery. Data represent means ± SEM.
[b]Cecal bilirubins and bile salts were extracted from 10–50 mg dry large intestinal contents.
[c]Symbols indicate statistically significant differences between ileectomized and ileal transected animals;
*p < 0.05,
‡p < 0.005

EXAMPLE 2

Zinc Salts Sequester Unconjugated Bilirubin (UCB) from Micellar Bile Salt (BS) Solutions in Vitro and Inhibit Enterohepatic Cycling of Bilirubin in the Hamster Introduction:

We showed recently that in ileal resected rats (Gastroenterology 1996; 110:1945–1957) and patients with Crohn's Disease (Gastroenterology 1996; 110:A159) total conjugated bilirubin levels are increased 2 to 3 fold in bile, consistent with enterohepatic cycling of UCB. We speculated that increased concentrations of BS in the colon solubilized UCB and facilitated its absorption. Contrariwise, increased intestinal binding of UCB should prevent its reabsorption. The purpose of this study was to investigate: 1) the precipitability of UCB solubilized in micellar BS solution by zinc salts ($ZnSO_4$, $Zn(OOCCH_3)_2$, $ZnCO_3$) known to be aqueous soluble at pH≦5.5, but sparingly soluble at pH 5.5–9.5; and 2) the influence of oral $ZnSO_4$ on total bilirubin secretion into bile of the hamster. UCB solutions (10 μM) were prepared with either 15 mM taurocholate (TC), glycocholate (GC) or 5 mM of the T or G conjugates of chenodeoxycholate and deoxycholate, respectively. Appropriate concentrations of the Zn salts (0–20 mM) were then added, and UCB remaining in solution was monitored by absorbance at 450 nm as functions of BS species, concentration, pH and time. Male Syrian golden hamsters, aged 12 weeks, were fed a chow diet (n=5) or a chow diet enriched with 1% $ZnSO_4$ (n=5), and bilirubin secretion rates were monitored during acute biliary diversion after 7 days.

The In Vitro Screening Assay

The reagents and procedure for performing the in vitro assay are described herein. All procedures were performed at room temperature (22° C.). The NaCl for the preparation of NaCl solutions was roasted at 600° C. to remove organic contaminants prior to use.

Reagent Preparation:

A UCB/taurocholate stock solution was prepared by dissolving an amount of solid UCB in 30 mM sodium taurocholate (purified, Sigma Chemical Corp., St. Louis, Mo.) in 0.15M NaCl, pH 8.0 to obtain a final concentration of 20 uM UCB. The UCB (bilirubin IXα, Porphyrin Products, Logan, Utah) should be at least grade A quality. The UCB quickly dissolved at pH 8.0 with the resultant UCB/taurocholate stock solution having a slightly lower pH.

Micelles form spontaneously at bile salt concentrations that are greater than the critical micellar concentration ("CMC"). The CMC for sodium taurocholate under these conditions is 3 mM. A 10 mM sodium taurocholate solution contains approximately 3 mM sodium taurocholate monomers and 7 mM sodium taurocholate micelles; each micelle contains about 3–4 molecules of sodium taurocholate. The UCB/taurocholate stock solution contains a molar ratio of UCB to sodium taurocholate of 1:1500. At this ratio, the micelle is unsaturated with UCB and, thus, essentially all UCB is located in the micelles. If alternative bile salts (e.g., taurodeoxycholate, taurochenodeoxycholate) are used for micelle formation, the relative concentrations of the bile salt and the UCB should be selected so that the micelles are unsaturated with UCB. Glycine conjugated bile salts are not preferred because they have a pKa in the range of pH 4–5. This condition ensures that zinc salt induced extraction of UCB from micelles truly is mediated by zinc salt adsorption of bilirubin that shifts the $bilirubin_{micelle} \leftrightarrows bilirubin_{zinc\ salt}$ equilibrium and induces the further extraction of bilirubin from the micelles.

A Zn salt stock solution was prepared by dissolving the appropriate zinc salt (or putative bilirubin binding agent) in 0.15M NaCl, pH 6.0–7.0 to obtain a final concentration of 10 mM zinc salt. It is preferred that the zinc salt be >99% pure. A pH that is less than about pH 7.0 is necessary to dissolve an appropriate zinc salt in aqueous solution. Appropriate zinc salts (e.g., zinc sulfate, zinc carbonate) can be obtained from Sigma Chemical Corp., St. Louis, Mo.; Fisher Scientific, Pittsburgh, Pa.; and Aldrich Chemical Corp., Milwaukee, Wis.

Procedure:

The assay was performed by admixing an equal volume of the UCB/taurocholate stock solution and the Zn salt stock solution to form a mixture. Typically, the mixture has a pH from about pH 6.0 to pH 7.0 and an $A_{450}=0.7$ (approximately). The pH of the mixture was adjusted to about pH 8.0 by adding about 1–2 μl of a 2M NaOH, and the $A_{450}$ of the mixture (at pH 8.0) solution phase ("supernatant") was determined. A mixture (at pH 8.0) supernatant has an $A_{450}=0.1$ (approximately). The adjustment of the mixture pH from about pH 6–7 to pH 8.0 resulted in the precipitation of the zinc salt as floccules; the solution phase ("supernatant") of this mixture is sufficiently separate from the floccules to allow an absorbance reading of the "supernatant" without the need for prior centrifugation or other separation. This pH-induced zinc salt precipitation was observed to be reversible if the pH of the mixture was subsequently reduced to pH 3–6 by addition of 1–2 μl of 2M HCl. Microscopic examination of the floccules showed that the floccules contained the amorphous zinc salt and that bilirubin was adsorbed to the surface of the zinc salt floccules.

Results and Conclusions:

In all BS systems, UCB was only slightly bound by Zn salts at pH ≦6.5, but became maximally precipitated (~90%) after 5 to 30 min. of incubation with ≧5 mM Zn salts between a pH of 6.8 and 9.0. By microscopy, the precipitates contained UCB bound to the surfaces of amorphous floccules of the Zn salt which crystallized slowly. When measured over 0–30 min. of acute biliary washout, total bilirubin secretion rates (mean±S.D.) were 36±6 nmol/hr/100 g B.W. in the control hamsters and 25±8 nmol/hr/100 g B.W. in the $ZnSO_4$ group (P≦0.03). Flocculated Zn salts at physiological pH adsorb UCB essentially completely from unsaturated BS micellar solutions, and suppress biliary bilirubin secretion in vivo, suggesting inhibition of enterohepatic cycling of UCB. This observation in intact hamsters suggests that enterohepatic cycling of UCB may be physiological in animals with predominantly monoconjugates of bilirubin. Since Zn is the least toxic of the trace metals, it is likely that its salts exhibit a prophylactic role in humans in inhibiting enterohepatic cycling of bilirubin associated with bile salt malabsorption, and therefore prevent pigment gallstone formation.

The above-described in vitro assay based on the extraction of bilirubin from BS micelles by zinc salts at physiological pH can be used as a simple, high throughput screening assay for testing putative adsorptive agents for their ability to adsorb bilirubin from BS micelles under conditions of physiological pH. Exemplary agents that have been or can be tested for their ability to adsorb bilirubin are provided in Table 4. According to this screening assay, the putative adsorptive agent is substituted for the zinc salt in the above-described assay and the extent of bilirubin extraction from the micelles is determined by monitoring absorbance at 450 nm as described. Preferably, zinc sulfate serves as a positive control in the screening assay. The in vitro assay is predictive of the in vivo ability of the binding agent to adsorb bilirubin in the gastrointestinal tract of the animal model. Accordingly, the in vitro assay provides a simple, high throughput screening assay for testing putative bilirubin binding agents that is predictive of an in vivo therapeutic activity. This assay has been used to assess the bilirubin absorption capability of a representative group of the agents of Table 4. The results of the screening assay indicate that the following agents were effective at absorbing bilirubin to a detectable extent in the screening assay: calcium carbonate, bismuth subnitrate, CholestaGel/RenaGel, Questran, activated carbon, Chlopromazine Hcl, Acacia, Carrageenan, Acetylsalicylic Acid, zinc sulfate, zinc chloride, zinc methacrolate, zinc acetate and cadmium acetate. The cadmium acetate reportedly is toxic in humans but was studied to determine whether transition metal salts other than zinc also could be used to effectively remove bilirubin in the high througput screening assay. The agents which were tested exhibited a range of bilirubin absorption activity. The agents which exhibited exceptionally high bilirubin absorption activity were the zinc salts, bismuth subnitrate, CholestaGel/RenaGel, Questran, activated carbon, Chlopromazine HCl and Acetylsalicylic Acid (aspirin). In view of these results, one of ordinary skill in the art would not reasonably question the usefulness of such compounds and, in particular, the usefulness of zinc salts or other transition metal salts for the purpose of removing bilirubin from a patient by absorption of a soluable bilirubin in the gastrointestinal tract.

TABLE 4

Categories of F.D.A.-Approved Drugs and Other Agents that Can be Screened for the Ability to Absorb Bilirubin using the in vitro Screening Assay of Example 2

I. Antacids:

| | | |
|---|---|---|
| a. | Aluminum Hydroxide | (Aludrox, Alternagel; Wyeth-Ayerst, Johnson & Johnson (J & J)•Merck) |
| b. | Calcium Carbonate (and acetate) | (Caltrate-600; Lederle) |
| c. | Calcium Phosphate | Dibasic (Dical D; Abbott) Tribasic (Posture-D; Whitehall) |
| d. | Magaldrate | (Riopan; Whitehall) |
| e. | Aluminum and Magnesium Hydroxides (± Simethicone) | (Maalox; Rhône-Poulenc-Rorer) |

TABLE 4-continued

Categories of F.D.A.-Approved Drugs and Other Agents that Can be Screened for the Ability to Absorb Bilirubin using the in vitro Screening Assay of Example 2

| | | |
|---|---|---|
| f. | Sucralfate | (Carafate; Marion-Merrell-Dow) |
| g. | Calcium Panthothenate | (Mega B; Arco) |
| h. | Bismuth subnitrate | |

II. Laxatives: (Bulk, Softeners, Mineral Oil, Osmotic, Stimulant)

| | | |
|---|---|---|
| a. | Sodium Docusate | (Dialose; J & J•Merck) |
| b. | Psyllium Hydrocolloid | (Effer-Sylliva; J & J•Merck; Metamucil; Procter & Gamble) |
| c. | Simethicone | (Mylanta Gas; J & J•Merck) |
| d. | Calcium & Magnesium Carbonates (± Simethicone) | (Mylanta Gel Caps; J & J•Merck) |

III. Antiflatulents:

| | | |
|---|---|---|
| a. | Charedal Plus | (Kramer) |
| b. | Flatulex (Simethicone & Activated Charcoal) | (Dayton) |
| c. | Mylanta Gas | (J & J•Merck) |
| d. | Mylicon Drops (Simethicone +) | (J & J•Merck) |

IV. Transition Metal Salts

| | |
|---|---|
| a. | Zn Sulfate, Zn Chloride, Zn Methacrylate, Zn Acetate |
| b. | Bismuth subnitrate (also an antacid) |
| c. | Cadmium Acetate |

V. Bile Acid Binders:

| | | |
|---|---|---|
| a. | Cholestagel/Renagel | (GelTex Inc.-in FDA Approval Process) |
| b. | Colestid Granules | (Cholestipol; Upjohn) |
| c. | Questran | (Cholestyramine; Bristol-Myers-Squibb) |

VI. Phenothiazines: (Anti-psychotics)

| | | |
|---|---|---|
| a. | Prochlorperazine HCl | (Compazine; Smith-Kline-Beecham) |
| b. | Trifluoperazine HCl | (Stelazine; Smith-Kline-Beecham) |
| c. | Chlorpromazine HCl | (Thorazine; Smith-Kline-Beecham) |

VII. Polybasic Antibiotics:

| | | |
|---|---|---|
| a. | Polymyxin B-$SO_4$ | (Burroughs Wellcome) |
| b. | Neomycin-$SO_4$ | (Biocraft) |
| c. | Gentamycin-$SO_4$ | (Schering) |
| d. | Aminoglycosides | (Amikacin; Bristol, Meyers, Squibb) (Netilmicin; Schering Plough) |

VIII. Gums and Fibers:

| | |
|---|---|
| a. | Acar/Acacia |
| b. | Carrageenan |
| c. | Pectins |
| d. | Cellulose/Hemicellulose |
| e. | Lignins |
| f. | Bran |

IX. Therapeutic Acids

| | |
|---|---|
| a. | Acetylsalicylic acid (aspirin) |
| b. | Salicylic acid |
| c. | 5-aminosalicylic acid |
| d. | Fusidic Acid |

I claim:

1. A method for removing bilirubin from a patient by adsorption of a soluble bilirubin in the gastrointestinal tract, the method comprising:

orally administering to the patient, a composition comprising a zinc salt, wherein the zinc salt is present: (i) in a therapeutically effective amount and (ii) in a form that is insoluble in the gastrointestinal tract.

2. The method of claim 1, further comprising the step of:
   selecting a patient having a disorder that is mediated by an excessive amount of an unconjugated bilirubin in the gastrointestinal tract.

3. The method of claim 2, wherein selecting comprises identifying an adult patient having a serum total bilirubin concentration greater than about 34.0 µmol/L.

4. The method of claim 3, wherein selecting comprises identifying an adult patient having a serum total bilirubin concentration from about 34.0 µmol/L to about 170 µmol/L.

5. The method of claim 2, wherein selecting comprises identifying an adult patient having a total gallbladder bile bilirubin concentration greater than about 3000 µmol/L.

6. The method of claim 5, wherein selecting comprises identifying an adult patient having a total gallbladder bile bilirubin concentration from about 3000 µmol/L to about 9000 µmol/L.

7. The method of claim 2, wherein the patient is diagnosed as having a disorder selected from the group consisting of: a gallstone disorder and a bile salt malabsorption disorder.

8. The method of claim 7, wherein the disorder is a gallstone disorder.

9. The method of claim 1, wherein the zinc salt is selected from the group consisting of a zinc sulfate, a zinc gluconate, a zinc acetate, a zinc aspartate, and zinc carbonate.

10. The method of claim 1, wherein the zinc salt is selected from the group consisting of zinc sulfate, zinc acetate and zinc carbonate.

11. The method of claim 1, wherein the zinc salt is contained in a pH-sensitive delivery vehicle that releases the zinc salt at a pH greater than about pH 7.0.

12. The method of claim 11, wherein the zinc salt is contained in a pH-sensitive delivery vehicle that releases the zinc salt at a pH from about pH 7.0 to about pH 9.0.

13. The method of claim 1, wherein a therapeutically effective amount of the composition contains an amount of the zinc salt that is sufficient to reduce the serum, total bilirubin concentration to less than about 34.0 µmol/L.

14. The method of claim 13, wherein the therapeutically effective amount of the composition contains an amount of zinc salt from about 100 mg/70 kg body weight to about 1 gm/70 kg body weight.

15. A method for decreasing a serum bilirubin concentration in a patient by adsorbing soluble bilirubin in the gastrointestinal tract, the method comprising:
   orally administering to the patient, a composition comprising a zinc salt, wherein the zinc salt is present: (i) in an amount sufficient to reduce the serum bilirubin concentration and (ii) in a form that is insoluble in the gastrointestinal tract.

16. A pharmaceutical composition comprising:
   (1) a zinc salt; and
   (2) a pharmaceutically acceptable carrier,
wherein the zinc salt is present: (i) in an amount sufficient to reduce an elevated serum bilirubin concentration and (ii) a form that is insoluble in the gastrointestinal tract.

17. The composition of claim 1, wherein the composition is contained in a delivery system that releases the zinc salt in the gastrointestinal tract.

18. The composition of claim 17, wherein the delivery vehicle comprises a pH sensitive delivery vehicle that releases the zinc salt at a pH greater than about pH 7.0.

19. The composition of claim 18, wherein the delivery vehicle comprises a pH sensitive delivery vehicle that releases the zinc salt at a pH from about pH 7.0 to about pH 9.0.

20. The composition of claim 17, wherein the delivery vehicle comprises a capsule or tablet having an enteric coating that is resistant to acidic pH and that is sensitive to basic pH.

* * * * *

UNITED STATES PATENT AND TRADEMARK OFFICE
CERTIFICATE OF CORRECTION

PATENT : 5,804,218
DATED : September 8, 1998
INVENTOR(S) : Martin C. Carey

It is certified that error appears in the above-identified patent and that said Letters Patent is hereby corrected as shown below:

Title page, insert the following item:

-- [60] Provisional application No.: 60/026,745, Sept. 26, 1996.--

Signed and Sealed this

Fifth Day of January, 1999

Attest:

Attesting Officer

*Acting Commissioner of Patents and Trademarks*